United States Patent
Song et al.

(10) Patent No.: US 11,261,271 B2
(45) Date of Patent: Mar. 1, 2022

(54) THERMOSENSITIVE PHOSPHAZENE-BASED POLYMER COMPRISING SULFATE MOIETY, AND PREPARATION METHOD AND USE THEREOF

(71) Applicant: KOREA INSTITUTE OF SCIENCE AND TECHNOLOGY, Seoul (KR)

(72) Inventors: Soo Chang Song, Seoul (KR); Bo Bae Seo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 154 days.

(21) Appl. No.: 16/536,907

(22) Filed: Aug. 9, 2019

(65) Prior Publication Data
US 2020/0048377 A1 Feb. 13, 2020

(30) Foreign Application Priority Data

Aug. 9, 2018 (KR) .................. 10-2018-0093018

(51) Int. Cl.
- *C08F 30/02* (2006.01)
- *A61L 27/16* (2006.01)
- *A61L 27/36* (2006.01)
- *A61L 27/52* (2006.01)

(52) U.S. Cl.
CPC .............. *C08F 30/02* (2013.01); *A61L 27/16* (2013.01); *A61L 27/3645* (2013.01); *A61L 27/52* (2013.01)

(58) Field of Classification Search
None
See application file for complete search history.

(56) References Cited

U.S. PATENT DOCUMENTS

| | | | |
|---|---|---|---|
| 6,235,061 B1* | 5/2001 | Laurencin | A61L 27/18 523/115 |
| 2009/0047348 A1* | 2/2009 | Song | A61P 43/00 424/486 |
| 2010/0298525 A1* | 11/2010 | Andrianov | C08G 79/025 528/321 |
| 2014/0031289 A1* | 1/2014 | Song | C08G 79/025 514/11.4 |

FOREIGN PATENT DOCUMENTS

| KR | 100259367 B1 | 6/2000 |
|---|---|---|
| KR | 100315630 B1 | 12/2001 |

* cited by examiner

Primary Examiner — Satya B Sastri
(74) Attorney, Agent, or Firm — Cantor Colburn LLP

(57) ABSTRACT

Provided is a thermosensitive phosphazene-based polymer including an amino acid ester moiety, a polyethyleneglycol moiety, and a moiety including a sulfate group linked directly or by a linker in a predetermined ratio, a method of preparing the same, and a hydrogel-formable composition including the same. For example, a hydrogel formed from the composition may be used for tissue regeneration or drug delivery or used as a storage, a body tissue regeneration inducer, or a filler in a body.

19 Claims, 16 Drawing Sheets

FIG. 1
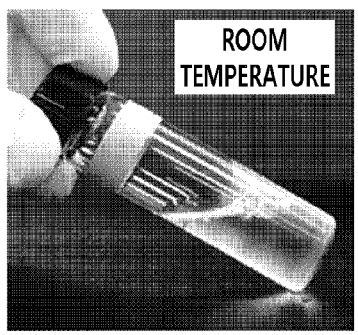
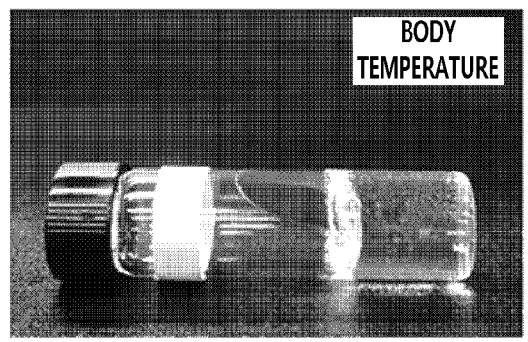 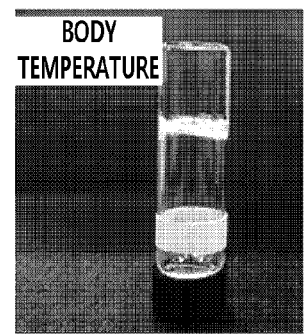

FIG. 6
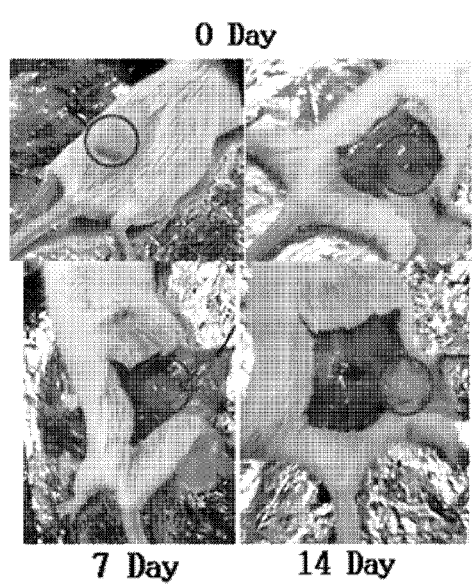
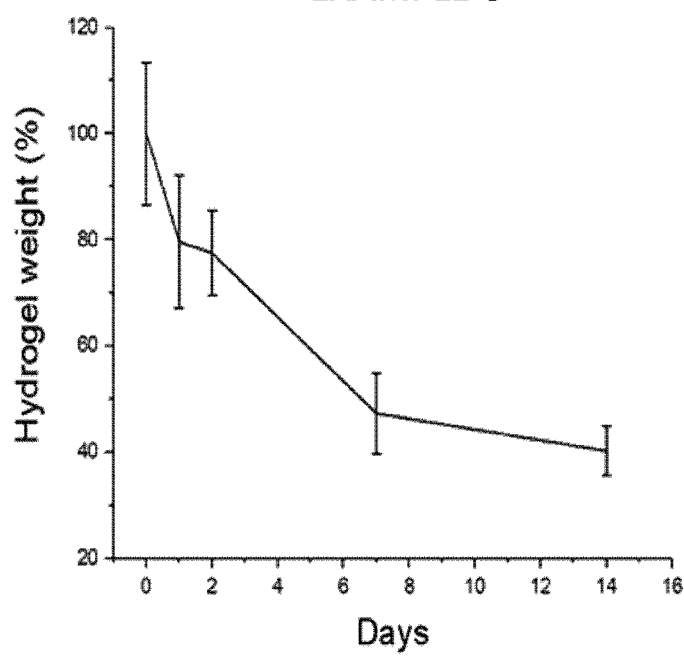

THERMOSENSITIVE PHOSPHAZENE-BASED POLYMER COMPRISING SULFATE MOIETY, AND PREPARATION METHOD AND USE THEREOF

This application claims priority to Korean application serial no. 10-2018-0093018 filed Aug. 9, 2018 in the Korean Patent Office under 35 U.S.C. § 119, the content of which is herein incorporated by reference in its entirety.

TECHNICAL FIELD

The present invention relates to a thermosensitive phosphazene-based polymer including an amino acid ester moiety, a polyethyleneglycol moiety, and a moiety including a sulfate group linked directly or by a linker in a predetermined ratio, a method of preparing the same, and a hydrogel-formable composition including the thermosensitive phosphazene-based polymer. For example, a hydrogel formed from the composition may be used for tissue regeneration or drug delivery or used as a storage, a body tissue regeneration inducer, or a filler in a body.

BACKGROUND ART

Thermosensitive polymers are polymers that exhibit a drastic change in their physical properties (shape, surface properties, solubility, and sol-gel transition) even with a small environmental change in temperature and may be used for drug delivery, tissue engineering, cell culture, and sensors.

Thermosensitive polymer hydrogel shows a sol-gel phase transition, where a liquid state, i.e., sol phase, maintained at a lower temperature turns to a gel phase as temperature increases. Thermosensitive polymer hydrogel injected in a liquid state may be uniformly distributed in a lesion regardless of the shape of tissue to which the hydrogel is applied and may immediately form a three-dimensional structure at a body temperature to effectively exist in a shape suitable for the lesion. Therefore, thermosensitive polymer hydrogel may be implanted into a desired region of a lesion by directly injecting the hydrogel thereinto without any invasive surgical operation.

As a result of extensive research, the present inventors have found that a phosphazene-based polymer obtained by substituting a dichlorophosphazene linear polymer with an amino acid ester and methoxypolyethyleneglycol has characteristics of a thermosensitive polymer exhibiting a sol-gel phase transition according to a temperature change in which the polymer exits in a liquid state below a predetermined temperature and forms a three-dimensional gel structure at a temperature higher than the predetermined temperature (Korean Patent Nos. 10-0259367 and 10-0315630).

Description of Embodiments

Technical Problem

An object of the present invention is to design and provide a novel phosphazene-based polymer not only capable of being loaded with hydrophobic drugs and/or various protein or peptide drugs including an ionic group but also capable of forming a hydrogel that absorbs, retains, and releases, in a sustained-release manner, a physiologically active substance secreted in a living body such as a hormone or a growth factor due to improved interaction with the physiologically active substance, at around a body temperature by modifying a biodegradable, thermosensitive phosphazene-based polymer.

Solution to Problem

It is a first aspect of the present invention to provide a thermosensitive phosphazene-based polymer including a sulfate group, wherein a first moiety of an amino acid ester represented by Formula 2 below, a second moiety of polyethyleneglycol represented by Formula 3 below, and a third moiety including a sulfate group linked directly or by a linker, are linked to a phosphorous atom of a polyphosphazene backbone represented by Formula 1 below, in a molar ratio of a:b:c respectively by —O— or —NH—.

[Formula 1]

[Formula 2]

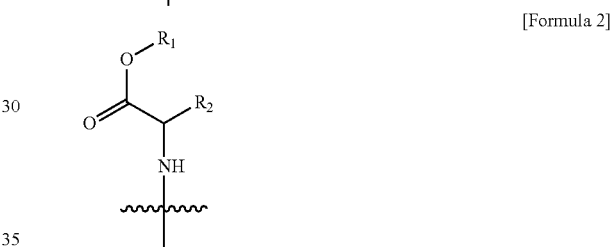

[Formula 3]

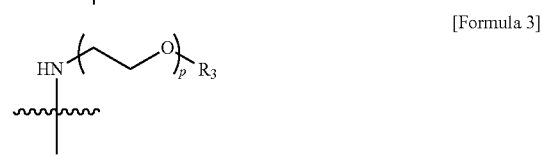

In the formulae, a is 55 mol % to 75 mol %, b is 5 mol % to 30 mol %, and c is 0.5 mol % to 20 mol %.

It is a second aspect of the present invention to provide a method of preparing the phosphazene-based polymer including a sulfate group according to the first aspect, the method including a first step of reacting polydichlorophosphazene represented by Formula 4 with an amino acid ester represented by Formula 5, a second step of further reacting the reaction mixture obtained from the first step by adding a hydrogen sulfate compound including a $C_{1-6}$ aminoalkanol or an amine group at one end to the reaction mixture, a third step of further reacting the reaction mixture obtained from the second step by adding aminopolyethyleneglycol to the reaction mixture, and a fourth step of reacting a product obtained from the third step with a sulfur trioxide or a composite thereof.

[Formula 4]

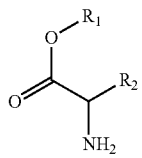
[Formula 5]

The second step and the third step may be performed in a reverse order, and

The fourth step may be omitted when the hydrogen sulfate compound including an amine group at one end is added in the second step.

It is a third aspect of the present invention to provide a composition including the thermosensitive phosphazene-based polymer including a sulfate group according to the first aspect and capable of forming a hydrogel.

It is a fourth aspect of the present invention to provide a hydrogel formed from the composition according to the third aspect.

Hereinafter, the present invention will be described in detail.

A thermosensitive polymer is a polymer exhibiting a drastic change in solubility according to a temperature change. As temperature increases, hydrogen bonds between the polymer and a solvent is weakened to cause dehydration and hydrophobic attractions between molecules of the polymer increase to form a more hydrophobic structure. Since polymer-polymer interactions and water-water interactions are preferred to the hydrogen bonds between the polymer and water at a low critical solution temperature (LCST), dehydration rapidly occurs in the polymer, resulting in formation of a more hydrophobic structure.

The LCST of the thermosensitive polymer varies according to the balance between hydrophobic groups and hydrophilic groups bound to a polymer backbone. In general, as the content of the hydrophilic groups increases, a phase transition temperature increases, while as the content of the hydrophobic groups increases, the phase transition temperature decreases.

As a result of designing a thermosensitive phosphazene-based polymer including a sulfate group represented by Formula 1, interestingly, the present inventors have found that the sulfate group contained in the polyphosphazene-based polymer may alleviate cytotoxicity caused by use of a high concentration of the polyphosphazene-based polymer (FIG. 7).

The phosphazene-based polymer, unlike organic polymers having a backbone of carbon-carbon bonds, has a backbone of conjugated bonds between inorganic elements of phosphorous (P) and nitrogen (N), and thus various substituents may be introduced thereinto and the phosphazene-based polymer may be degraded in a living body. It was identified that the phosphazene-based polymer including an amino acid ester, polyethyleneglycol, and a sulfate group introduced directly or by a linker in a predetermined ratio according to the present invention may provide a hydrogel capable of promoting tissue regeneration since the phosphazene-based polymer turns into a hydrogel state in a living body when injected thereinto in a solution state due to sol-gel transition occurring at around a body temperature and forms a hydrogel that is loaded with a drug contained in the solution and release the drug in a sustained-release manner or a hydrogel that absorbs, retains, and releases a hormone or a growth factor secreted in the living body even when the solution does not contain a drug. The present inventors have also found that a hydrogel formed of the phosphazene-based polymer including a sulfate group instead of a carboxyl group according to the present invention has higher regeneration efficiency than a hydrogel formed of the phosphazene-based polymer alone, a hydrogel formed of the polymer and a growth factor, a hydrogel formed of the polymer and a stem cell, a hydrogel formed of the polymer, the growth factor, and the stem cell, natural regeneration, a growth factor alone, or a stem cell alone (FIGS. 12 to 16). The present invention is based thereon.

According to the present invention, in the thermosensitive phosphazene-based polymer including a sulfate group, the first moiety of an amino acid ester represented by Formula 2 below, the second moiety of polyethyleneglycol represented by Formula 3 below, and the third moiety including a sulfate group linked directly or by a linker, are linked to a phosphorous atom of a polyphosphazene backbone represented by Formula 1 below, in a molar ratio of a:b:c respectively by —O— or —NH—.

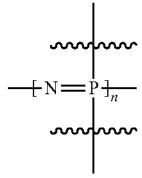
[Formula 1]

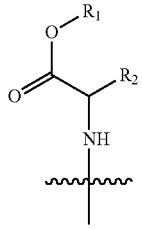
[Formula 2]

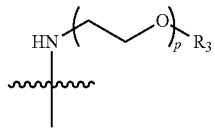
[Formula 3]

Here, a is 55 mol % to 75 mol %, b is 5 mol % to 30 mol %, and c is 0.5 mol % to 20 mol %.

In the formulae, $R_1$ is $C_{1-6}$ alkyl, $C_{1-6}$ alkenyl, or $C_{6-10}$ aryl-$C_{1-6}$ alkyl;

$R_2$ is hydrogen, methyl, isopropyl, 1-methylpropyl, 2-methylpropyl, thiomethyl, methylthioethyl, benzyl, hydroxybenzyl, or 2-indolylmethyl;

$R_3$ is $C_{1-6}$ alkyl;

n is an integer of 3 to 100,000; and p is an integer of 1 to 20

The polyphosphazene backbone of Formula 1 has 2n substitution sites, all or a part of which may be substituted with the first to the third moieties. For example, the n may be an integer of 100 to 10,000, but is not limited thereto.

The sulfate group-containing phosphazene-based polymer according to the present invention may have a much stronger negative charge than a phosphazene-based polymer including the same mol % of carboxyl group (Experimental Example 2, FIG. 4). As shown in FIG. 5, the phosphazene-based polymer of the present invention may have a surface charge varying according to a substitution degree of the sulfate group.

Thus, although polymers are composed of the same substituents (Examples 1 to 2), gel properties thereof (initial gelation temperature and gel strength at body temperature) may be adjusted according to the ratio of the respective substituents (a, b, c) (Table 1).

Furthermore, the sulfate group-containing phosphazene-based polymer hydrogel according to the present invention may be designed to achieve biodegradability further to have an adjusted in vivo degradation rate (FIG. 6). In the case of designing the phosphazene-based polymer of the present invention as a biodegradable polymer, the following advantages may be obtained when applied to a drug delivery system: (i) A surgical operation to remove the polymer is not necessary since the polymer is degraded in the body after being administered to a patient as a drug carrier, and (ii) Dissolution of the drug is affected by degradation of the biodegradable polymer.

In order to prevent degradation products derived from the first moiety of Formula 2 from being toxic in the body when the thermosensitive phosphazene-based polymer according to the present invention is degraded in the body, the types of $R_1$ and/or $R_2$ may be adjusted to mimic natural amino acids. In addition, the degrees of hydrophobicity of $R_1$ and/or $R_2$ may be each independently adjusted to participate hydrophobic interactions.

Regarding the second moiety of polyethyleneglycol represented by Formula 3, PEG is not toxic in the living body among substances that may exhibit hydrophilicity. PEG chains are involved in sol-gel phase transition according to temperature by hydrogen bonds with water. In addition, since PEG is distributed to surround the surface of the hydrogel, the hydrogel or a small amount of degradation product of the hydrogel may not aggregate with proteins in the body. That is, the PEGylation effect may be obtained in the sulfate group-containing phosphazene-based polymer hydrogel according to the present invention.

For example, the polyethyleneglycol second moiety may be a polymer moiety having a weight average molecular weight of 300 to 3000 such that a final polymer has biodegradability and thermosensitivity, but is not limited thereto.

For example, in the sulfate group-containing phosphazene-based polymer according to the present invention, $R_1$ may be methyl, ethyl, propyl, butyl, benzyl, or 2-prophenyl and $R_3$ may be methyl, without being limited thereto.

For example, phosphazene-based polymer including a sulfate group according to the present invention may be a polymer having a weight average molecular weight Mw of 500 to 100,000, for example, a polymer having a weight average molecular weight of 1,000 to 50,000, without being limited thereto.

In addition, the sulfate group-containing phosphazene-based polymer according to the present invention may further include a fourth moiety having a functional moiety for introducing a function group into an end of the polymer. The functional moiety may be a hydroxyl group or a carboxyl group, without being limited thereto. Furthermore, the polymer may further include a fourth' moiety at least one functional substance linked directly or by a linker to a part of or the entire functional group of the fourth moiety, wherein the functional substance is selected from the group consisting of a substance capable of regulating a degradation rate of the polymer, a substituent including an ionic group capable of regulating a degradation rate, a substituent capable of cross-linking, an additional compound capable of inducing tissue adhesion, a physiologically active substance, and a composite material formed by linear connection of two or more substances thereof.

Furthermore, the functional moiety and/or the functional substance linked thereto may be in a form protected with a protecting group.

Examples of the substance capable of regulating the degradation rate of the polymer may be, but are not limited to, amino acids, peptides, and depsipeptide esters.

The substituent including an ionic group capable of regulating the degradation rate may be a substituent including a dicarboxylic acid-based compound having 3 to 30 carbon atoms, specifically 3 to 9 carbon atoms, more specifically 3 to 6 carbon atoms linked via a hydroxyl group-containing divalent functional moiety, or $NH_2CH(SH)CO_2H$, $NH_2(CH_2)_qSH$, $NH_2(CH_2CH_2NH)_rH$, $[NH_2CH(C_4H_8NH_2)CO]_rOH$, $[NH_2CH[(CH_2)_3C(=NH)(NH_2)]CO]_rOH$, $[OCH_2CH_2CH_2CH_2CH_2N(CH_2CH_2CO_2CH_2CH_2)_2]_r$, folic acid, hyaluronic acid, cyclodextrin, an imidazole-based compound, an anticancer agent, histidine, lysine, arginine, cysteine, thiolalkylamine (e.g., having 1 to 50 carbon atoms), spermine, spermidine which are additionally linked thereto, polyethyleneimie, polyhistidine, polylysine, and polyarginine having various weight average molecular weights, protamine, heparin, chitosan, protamine, or a peptide including 1 to 20 amino acids, e.g., an RGD or RGD derivative (a peptide consisting of 4 to 5 amino acids including RGD, such as RGDS, RGDY, GRGDS, and GRGDY.

The substituent capable of cross-linking may include a substituent capable of forming a chemical cross-link or a cross-link caused by ultraviolet radiation, the presence of a cross-linking agent and/or an additive, or an enzyme, without limitation. For example, the substituent capable of cross-linking may be a compound having a thiol group or a vinyl group, or a compound having tyramine, tyrosine, or a phenyl derivative such as an acrylate-based compound, a methacrylate-based compound, an acrylaminde-based compound, a vinylsulfone-based compound, a thiol-based compound, a cystein-based compound, a cysteamine-based compound, a mercaptic acid-based compound, and an allyl pyrimidine-based compound.

The additional compound capable of inducing tissue adhesion may be a substituent including a cyanoacrylate-based compound used as a functional group for conventional tissue adhesion.

The physiologically active substance may be a drug, such as a protein, a polypeptide, a peptide, an antibody, a fusion protein, a hormone, a vaccine, a gene, an anticancer agent, or an angiogenesis inhibitor, without being limited thereto.

Specifically, the sulfate group-containing phosphazene-based polymer of the present invention may be a phosphazene-based polymer including a sulfate group represented by a formula poly[(isoleucineethylester)$_a$(aminomethoxypolyethyleneglycol 750)$_b$(aminoethylsulfate)$_c$phosphazene]$_n$, and having a weight average molecular weight of 15,000 to 37,000.

In the formula,
a' is 1.1 to 1.5,
b' is 0.1 to 0.6,
c' is 0.01 to 0.4,
1.6≤a'+b'+c'≤2, and
n' is an integer of 3 to 100,000.

The polymer may further include ethyl-2-(O-glycyl)lactate, aminoethylglytarate, aminoethyladipate, or the like, as the functional moiety for introducing a function group to an end of the polymer enabling introduction of the substance capable of regulating the degradation rate of the polymer, the substituent including an ionic group capable of regulating a degradation rate, the substituent capable of cross-linking, the additional compound capable of inducing tissue adhesion, the physiologically active substance, or the composite material formed by linear connection of two or more substances thereof, within about 20% based on the total number of moles of the entire moiety.

Meanwhile, the method of preparing the sulfate group-containing phosphazene-based polymer according to the present invention includes:

a first step of reacting polydichlorophosphazene represented by Formula 4 with an amino acid ester represented by Formula 5;

a second step of further reacting the reaction mixture obtained from the first step by adding a $C_{1-6}$ aminoalkanol or a hydrogen sulfate compound including an amine group at one end to the reaction mixture;

a third step of further reacting the reaction mixture obtained from the second step by adding aminopolyethyleneglycol to the reaction mixture; and a fourth step of reacting a product obtained from the third step with a sulfur trioxide or a composite thereof.

[Formula 4]

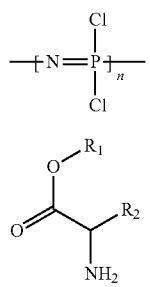

[Formula 5]

In the formulae, $R_1$, $R_2$ and n are as defined above, the second step and the third step may be performed in a reverse order, and the fourth step may be omitted when the hydrogen sulfate compound including an amine group at one end is added in the second step.

In the first step, the amino acid ester represented by Formula 5 may be used in a form including an amine group and an alkyl group having an ester group for the COOH group to prevent further reaction between amino acids.

For example, the amino acid ester may be isoleucine ethyl ester; the $C_{1-6}$ aminoalkoxypolyethyleneglycol may be aminomethoxypolyethyleneglycol; the $C_{1-6}$ aminoalkanol may be aminoethanol; dicarboxylic acid and an anhydrate thereof may be succinic acid, glutaric acid, adipic acid, or an anhydride thereof; and the di($C_{1-6}$ alkyl)carbodiimide may be diisopropylcarbodiimide.

The aminopolyethyleneglycol used in the second step may be obtained by substituting polyethyleneglycol having —OH groups with amine groups (—NH) by a 3-step process. Since polyethyleneglycol having —NH groups has higher reactivity and more selectively react than moisture than that having —OH groups, use of polyethyleneglycol substituted with —NH groups may be preferable.

In the preparation method of the sulfate group-containing phosphazene-based polymer of the present invention, the amino acid ester moiety, the alkoxyalkoxypolyethyleneglycol, and the sulfate group linked directly or by a linker may be introduced into the polyphosphazene backbone through the first to third steps.

For example, in the preparation method of the present invention, the first to third steps may be performed in a tetrahydrofuran solution in the presence of triethylamine, without being limited thereto.

In the preparation method of the present invention, tetrahydrofuran selected as a solvent may dissolve all reactants used, and accordingly, a homogeneous solution may be provided. Therefore, by omitting separating and purifying processes between the steps and continuously carrying out reactions, the reaction efficiency may be improved. However, the available solvent is not limited to tetrahydrofuran and various solvents known in the art may also be used without limitation as long as all of the reactants used are efficiently and completely dissolved therein. Alternatively, the preparation according to the present invention may be performed via a series of independent reactions using a solvent optimized for each step.

Furthermore, the reaction may be performed by including triethylamine in the first to third steps, and thus problems caused by generation of chlorine gas may be prevented because triethylamine holds chlorine gas generated during the reaction. This is merely an example, and the reaction is not limited to only triethylamine. That is, various substances may be used as long as the substances may hold chlorine gas during the reaction.

For example, the first step may be carried out for 18 to 60 hours while increasing a temperature from a range of −80 to −50° C. to a range of 20 to 60° C., without being limited thereto.

Since the amino acid $C_{1-6}$ alkyl ester, a reactant of the first step, is highly reactive with a polyphosphazene backbone, intensive reaction therebetween may occur even at room temperature so that the amino acid $C_{1-6}$ alkyl ester may bind to the polyphosphazene backbone in an agglomerate form without being uniformly bind thereto. Thus, uneven bonding caused by such explosive reaction may be prevented by initiating the reaction at a lower temperature of −80° C. to −50° C. Thereafter, the temperature may be increased to 20° C. to 60° C. as the reaction progresses, thereby allowing the remaining reactants to be completely reacted.

The reaction time is not limited as long as the reaction may sufficiently be carried out, and may appropriately be adjusted according to the reaction temperature. For example, as the reaction time decreases, reactants may remain because the reaction is not completed, whereas as the reaction time increases, time and/or energy may be unnecessarily wasted with a longer reaction time.

For example, each of the second and third steps may be independently carried out by cooling the reaction mixture to room temperature, e.g., a temperature of 10° C. to 30° C., after the previous step performed at the elevated temperature, adding reactants thereto, heating the reaction mixture to a temperature of 35° C. to 60° C., and performing reaction for 18 to 60 hours, without being limited thereto. Alternatively, the second and third steps may be performed in a 2-step process by adjusting temperature, i.e., at room temperature for 24 hours and then at a temperature of 40° C. to 50° C. for 24 hours, without being limited thereto.

As described above, in order to prevent non-uniform reaction caused by an explosive reaction while ultimately allowing reactants to be completely reacted, the reaction may be completed by reacting the same at a relatively low temperature for a certain period of time, followed by progressing the additional reaction by raising the temperature.

In order to efficiently carry out the reaction and to increase yield and purity of a product, the preparation method according to the present invention may further include a step a of removing triethylamine hydrochloride by filtering the reaction mixture before the fourth step. Furthermore, the preparation method according to the present invention may further include a step b of purifying the product after the step a, without being limited thereto. Through the additional series of processes, substances unnecessary for the subsequent reactions may be removed from the reaction mixture, and the product may be purified, thereby inducing a more efficient reaction and increasing the yield.

For example, the step b of purifying an intermediate product may be carried out by concentrating the reaction mixture of the previous step, dissolving the concentrated solution in tetrahydrofuran, inducing precipitation by adding an excess of hexane thereto, dissolving the precipitates in methanol, and dialyzing the resulting concentrate with methanol and water, without being limited thereto.

In the preparation method of the present invention, sulfur trioxide used in the fourth step may be provided in a complex form with the tertiary amine-based compound, without being limited thereto. The tertiary amine-based compound may include a nitrogen compound which behaves like tertiary amine in chemical reactions without limitation. Examples of the sulfur trioxide complex available in the preparation method according to the present invention may include sulfur trioxide pyridine complex, sulfur trioxide N,N-dimethylformamide complex, sulfur trioxide trimethylamine complex, and sulfur trioxide N-ethyldiisopropylamine complex.

Meanwhile, when the reaction is performed with the hydrogen sulfate compound including an amine group at one end in the second step, a compound substituted with a sulfate group is directly introduced into the polyphosphazene backbone in the second step, and thus the fourth step may be omitted. Examples of the hydrogen sulfate compound may include [carbamoyl(sulfooxy)amino]hydrogen sulfate, 2-amino-2-methylpropyl hydrogen sulfate, and amino hydrogen sulfate, but are not limited thereto. The shape and length of chains and/or the existence of another substituent are not limited as long as the compound includes an amine group to be directly linked to the polyphosphazene backbone and the object of introducing a sulfate group is achieved.

For example, in the preparation method of the present invention, the fourth step may be performed in a solution of tetrahydrofuran and dimethylformamide at a temperature of 20° C. to 50° C. for 18 to 60 hours, without being limited thereto. In the fourth step, reaction temperature and/or reaction time may be appropriately adjusted in consideration of reactivity between each reactant and the polyphosphazene backbone and completeness of the reaction in the same manner as the previous steps.

The third step may further include a step of filtering the reaction mixture obtained after adding dropwise a $C_{1-6}$ aminoalkoxypolyethyleneglycol solution to the reaction mixture of the second step, performing reaction, concentrating the filtrate under reduced pressure, dissolving the concentrate in methanol and dialyzing the resultant with methanol and water. The dialysis may be performed independently with each of the solvents for 3 to 7 days, e.g., for 5 days, without being limited thereto.

It is another aspect of the present invention to provide a composition capable of forming a hydrogel comprising the thermosensitive phosphazene-based polymer including a sulfate group according the present invention.

The composition capable of forming a hydrogel according to the present invention may be in a solution state at room temperature but may be converted from a sol state into a gel state at the body temperature. Thus, the hydrogel-formable composition according to the present invention may further include a substance to be carried (e.g., drug) and form a hydrogel loaded with the substance to be carried in a body. Although the sulfate group-containing polyphosphazene-based polymer according to the present invention includes a steroid drug (Experimental Example 5) or a protein drug (Experimental Example 6), characteristics of sol-gel transition in accordance with temperature change may be maintained and a similar viscosity variation behavior at a temperature at the time of injection and body temperature is observed. Since selection and use of drugs to be carried are not limited and it is predicted that the sol-gel phase transition characteristics are not considerably changed, the sulfate group-containing phosphazene-based polymer according to the present invention is advantageous to be used as a flatform system.

Also, the hydrogel formed from the composition according to the present invention may absorb water, an inorganic ion, a vitamin, a hormone, or a growth factor in a gel. Thus, the hydrogel formed from the composition according to the present invention may assist tissue regeneration. For example, since the hydrogel may absorb a substance such as a hormone or a growth factor secreted in the living body via interactions and maintain a high concentration of the substance in a target region, differentiation of stem cells nearby may be promoted, thereby improving tissue regeneration although a drug is not included in the hydrogel composition.

When the hydrogel-formable composition including the sulfate group-containing phosphazene-based polymer according to the present invention is prepared in an aqueous solution, the solution phase at room temperature gelates by incubation at 37° C. similar to the body temperature, indicating that a hydrogel may be formed in the body by injecting the hydrogel composition in an aqueous solution state into a lesion without surgical operation. Therefore, the hydrogel-formable composition according to the present invention may maximize therapeutic effects of a drug by concentrating the drug at a particular lesion in the human body and minimize side effects caused by using a highly toxic drug. Also, when a molecular imaging probe was used as a substance to be carried, a treatment process may be monitored in real time by imaging the probe by non-invasive in vivo imaging simultaneously with drug delivery.

Examples of the drug to be carried in the hydrogel-forming composition according to the present invention may include, but are not limited to, a therapeutic agent, a diagnostic agent, and a detection agent. Examples of the therapeutic agent may include, but are not limited to, an antibody, an antibody fragment, a drug, a medicine, a toxin, a nuclease, a hormone, an immunomodulator, a chelator, a boron compound, a photoactive agent or dye, and a radioactive isotope. Examples of the diagnostic agent/detection agent may include, but are not limited to, a radioactive isotope, a dye (e.g., biotin-streptavidin complex), a contrast agent, a fluorescent compound or molecule, and a contrast enhancing agent (paramagnetic ion) of magnetic resonance imaging (MRI).

For example, in the hydrogel-formable composition according to the present invention, the thermosensitive phosphazene-based polymer including a sulfate group according to the present invention may be in the form of a polymer solution in which the polymer is dissolved in a solvent such as water, a buffer solution, an acidic solution, a basic solution, a salt solution, physiological saline, water for injection, and dextrose saline at a concentration of 1 wt % to 50 wt %, preferably 3 wt % to 20 wt %.

Furthermore, when the hydrogel-forming composition according to the present invention further includes a hydrophobic drug, e.g., synthetic medicine, in a solution, the drug is contained in a polymer hydrogel formed in the body via bonds with a hydrophobic portion of the drug and the polymer hydrogel may serve as a sustained-release drug carrier and/or tissue growing implant.

In addition, a hydrogel loaded with a substance to be carried such as a drug may not only release the substance to be carried but also more efficiently control the drug release behavior than a polymer hydrogel into which the sulfate group is not introduced or a polymer hydrogel having a carboxyl group exhibiting the same effects by introducing the sulfate into the phosphazene-based polymer of the present invention (FIGS. 10 and 11).

For example, the phosphazene-based polymer of the present invention may control a release amount of a cationic drug in the body over time by including the sulfate group (Experimental Examples 7 and 8 and FIGS. 10 and 11). A substance to be carried that is cationic in a pH 7.4 environment may ionically interact with the sulfate group contained in the phosphazene-based polymer hydrogel of the present invention that is anionic in the same pH environment, so that the cationic substance to be carried may be trapped in the hydrogel for a long time.

The hydrogel-forming composition according to the present invention may further include a phosphazene-based polymer including a carboxyl group. The sulfate group and/or the carboxyl group which are negatively charged attract water molecules, and further attract sodium ions, thereby collecting a larger amount of water by osmosis. The phosphazene-based polymer of the present invention may provide a formulation released at a desired time with a desired release amount by adjusting the release amount of the cationic drug with time by controlling the content of the sulfate group, and adjusting the amounts of the —COOH group and the sulfate group as substituents in the phosphazene-based polymers and the composition thereof. Thus, the sulfate group-containing phosphazene-based polymer hydrogel according to the present invention may retain various biologically effective factors and control sustained-release thereof via ionic interactions according to types and degrees of surface charges of the polymer.

The sulfate group-containing phosphazene-based polymer hydrogel according to the present invention may serve as a body tissue prosthesis; a filter capable of controlling passage of molecules or particles in a body; a storage of water, an inorganic ion, a vitamin, and a hormone; and/or a body tissue regeneration inducer or a filler in the body.

Advantageous Effects of Disclosure

The sulfate group-containing phosphazene-based polymer according to the present invention has thermosensitivity and the ability to load a drug and/or perform release-release thereof, and thus the polymer may be efficiently applied to a lesion without a surgical operation since the polymer including or non-including a drug injected in a liquid state gelates at the body temperature, may be loaded with a synthetic drug including a hydrophobic portion for hydrophobic interactions, may be loaded with various protein or peptide drugs including an amine group via ionic interactions, and may be efficiently used for tissue regeneration without using a drug since the hydrogel may absorb and retain a hormone or a growth factor in the body via interactions therewith.

BRIEF DESCRIPTION OF DRAWINGS

FIG. 1 shows photographs of a solution of a sulfate group-containing phosphazene-based polymer prepared in Example 3 dissolved in phosphate-buffered saline (pH 7.4) at 4° C. at a concentration of 10 wt % obtained by visual observation of a sol-gel behavior thereof.

FIG. 6 shows photographs and a graph illustrating an in vivo degradation rate of a hydrogel of a sulfate group-containing phosphazene-based polymer prepared according to Example 3.

BEST MODE

Figure 2:
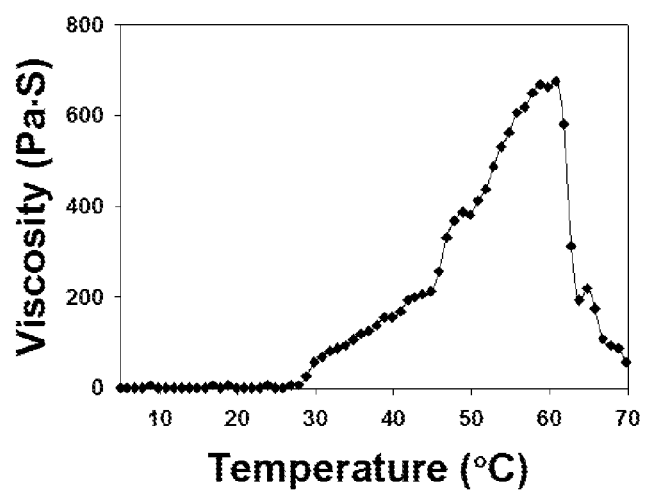
FIGS. 2 and 3 are graphs showing viscosities of solutions of sulfate group-containing phosphazene-based polymers (Examples 3 and 11) according to the present invention dissolved in phosphate-buffered saline (pH 7.4) at 4° C. at a concentration of 10 wt % measured with respect to temperature, respectively.

Hereinafter, the present invention will be described in more detail with reference to the following examples. However, these examples are for illustrative purposes only, and the present disclosure is not intended to be limited by these examples.

<Identification of Compounds>

In the examples below, element analysis of carbon, hydrogen, and nitrogen was carried out using Perkin-Elmer's C, H, and N analyzers in the Advanced Analysis Center of the Korea Institute of Science and Technology (KIST) in order to identify synthesized polymers. In addition, the nuclear magnetic resonance spectrum with hydrogen and phosphorus was measured by a Varian Gemini-300, and the weight average molecular weight Mw was measured by gel permeation chromatography using a Waters 1515 pump and a 2410 differentiation refractometer.

Example 1

Preparation of Poly[(isoleucineethylester)$_{1.38}$(aminomethoxypolyethyleneglycol 750)$_{0.57}$(aminoethylsulfate)$_{0.05}$phosphazene]$_n$ Dry isoleucine ethyl ester hydrochloride (IleOEt⸱HCl, 11.65 g, 59.53 mmol) was dissolved in 200 mL of anhydrous tetrahydrofuran (THF) including 35 mL of triethylamine. A solution prepared by dissolving polydichlorophosphazene (5 g, 43.14 mmol) in 50 mL of anhydrous THF was added dropwise to the mixed solution in an acetone-dry ice bath, and then the temperature was gradually raised to 40° C. to 50° C. and reaction was performed for 24 hours. After cooling the reaction mixture to room temperature, dry aminoethanol (0.94 g, 15.53 mmol) was dissolved 100 mL of in anhydrous THF and 5 mL of triethylamine was added to the reaction mixture, and then reaction was performed at a temperature of 40° C. to 50° C. for 24 hours.

After cooling the reaction mixture to room temperature, a solution prepared by dissolving dry polyethyleneglycol (6.47 g, 8.63 mmol) having a molecular weight of 750 in 200 mL of anhydrous THF and adding 5 mL of triethylamine thereto was added to the reaction mixture, and reaction was performed for 24 hours at a temperature of 40° C. to 50° C.

The solution in which the reaction was completed was filtered in order to remove produced triethylamine hydrochloride, and the reaction filtrate was concentrated under reduced pressure until a small amount of the solvent remained. The concentrated solution was dissolved in 10 mL of anhydrous THF, and then an excess of hexane was added thereto to induce precipitation. After repeating this process twice or three times, the precipitates were dissolved in a small amount of methanol, placed in MWCO 12000 membrane (Spectrum Laboratories, Inc.), dialyzed against methanol at room temperature for 4 days, dialyzed against distilled water for 4 days, and dried at a low temperature to obtain a polyphosphazene polymer [NP(IleOEt)$_{1.38}$(AMPEG750)$_{0.57}$(Aminoethanol)$_{0.05}$]$_n$ (7.21 g) including isoleucineethylester, aminomethoxypolyethyleneglycol, and aminoethanol.

The polyphosphazene polymer [NP(IleOEt)$_{1.38}$(AMPEG750)$_{0.57}$(Aminoethanol)$_{0.05}$]$_n$ obtained in the previous step was dissolved in 200 mL of anhydrous THF and 200 mL of dimethylformamide, and a solution prepared by dissolving sulfur trioxide pyridine complex (4.97 g, 31.25 mmol) in 200 mL of dimethylformamide was added to the reaction solution, and reaction was performed at a temperature of 25° C. to 40° C. for 24 hours. The reaction solution was filtered and the filtrate was concentrated under reduced pressure until a small amount of the solvent remained. The concentrated solution was placed in MWCO 1200 membrane, dialyzed against methanol for 4 days, dialyzed against distilled water for 4 days, and dried at a low temperature to obtain a final product [NP(IleOEt)$_{1.38}$(AMPEG750)$_{0.57}$(Aminoethylsulfate(AES))$_{0.05}$]$_n$.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.4-1.8(b, —NHC$\underline{H}$(C$\underline{H}$(CH$_3$)CH$_2$CH$_3$)COOCH$_2$CH$_3$),
δ 2.67-3.2(b, —NHCH$_2$C$\underline{H_2}$SO$_4$, —NH(CH$_2$CH$_2$O)$_{16}$C$\underline{H_3}$),
δ 3.4(s, —NH(CH$_2$CH$_2$O)$_{16}$C$\underline{H_3}$),
δ 3.4-3.9(b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$),
Average molecular weight (M$_w$): 2,200

Example 2

Preparation of Poly[(isoleucineethylester)$_{1.35}$(aminomethoxypolyethyleneglycol 750)$_{0.5}$(aminoethylsulfate)$_{0.15}$phosphazene]$_n$ A final product [NP(IleOEt)$_{1.35}$(AMPEG750)$_{0.5}$(AES)$_{0.15}$]$_n$ was obtained in the same manner as in Example 1, except that the amounts of isoleucine ethyl ester hydrochloride (10.97 g, 56.08 mmol), polydichlorophosphazene (5 g, 43.14 mmol), aminoethanol (0.79 g, 12.94 mmol), polyethyleneglycol (12.94 g, 17.26 mmol) having a molecular weight of 750, sulfur trioxide pyridine complex (3.78 g, 23.74 mmol), dimethylformamide (total 400 mL), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.4-1.8(b, —NHC$\underline{H}$(C$\underline{H}$(CH$_3$)CH$_2$CH$_3$)COOCH$_2$CH$_3$),
δ 2.67-3.2(b, —NHCH$_2$C$\underline{H_2}$SO$_4$, —NH(CH$_2$CH$_2$O)$_{16}$C$\underline{H_3}$),
δ 3.4(s, —NH(CH$_2$CH$_2$O)$_{16}$C$\underline{H_3}$),
δ 3.4-3.9(b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$),
Average molecular weight (M$_w$): 1900

Example 3

Preparation of Poly[(isoleucineethylester)$_{1.32}$(aminomethoxypolyethyleneglycol 750)$_{0.38}$(aminoethanol)$_{0.1}$(aminoethylsulfate)$_{0.2}$phosphazene]$_n$ A final product [NP(IleOEt)$_{1.3}$(AMPEG750)$_{0.4}$(Aminoethanopal)$_{0.1}$(AES)$_{0.3}$]$_n$ was obtained in the same manner as in Example 1, except that the amounts of isoleucine ethyl ester hydrochloride (11.15 g, 56.98 mmol), polydichlorophosphazene (5 g, 43.14 mmol), aminoethanol (0.79 g, 12.94 mmol), polyethyleneglycol (12.30 g, 16.4 mmol) having a molecular weight of 750, sulfur trioxide pyridine complex (3.86 g, 24.24 mmol), dimethylformamide (total 400 mL), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)CH$_2$CH$_3$)COOCH$_2$CH$_3$),
δ 1.4-1.8(b, —NHC$\underline{H}$(C$\underline{H}$(CH$_3$)CH$_2$CH$_3$)COOCH$_2$CH$_3$), δ 2.67-3.2(b, —NHCH$_2$CH$_2$SO$_4$, —NH(CH$_2$CH$_2$O)$_{16}$CH$_3$),
δ 3.4(s, —NH(CH$_2$CH$_2$O)$_{16}$CH$_3$),
δ 3.4-3.9(b, —NH(CH$_2$CH$_2$O)$_{16}$CH$_3$, —NHCH(CH(CH$_3$)CH$_2$CH$_3$)COOCH$_2$CH$_3$),
δ 3.9-4.3(b, —NHCH(CH(CH$_3$)CH$_2$CH$_3$)COOCH$_2$CH$_3$),
Average molecular weight (M$_w$): 2600

Example 4

Preparation of Poly[(isoleucineethylester)$_{1.23}$(aminomethoxypolyethyleneglycol 550)$_{0.57}$(aminoethylsulfate)$_{0.2}$phosphazene]$_n$ A final product [NP(IleOEt)$_{1.23}$(AMPEG550)$_{0.57}$(AES)$_{0.2}$]$_n$ was obtained in the same manner as in Example 1, except that polyethyleneglycol having a molecular weight of 550 was used instead of polyethyleneglycol having a molecular weight of 750, and the amounts of isoleucine ethyl ester hydrochloride (10.38 g, 53.07 mmol), polydichlorophosphazene (5 g, 43.14 mmol), aminoethanol (0.53 g, 8.63 mmol), polyethyleneglycol (13.53 g, 24.6 mmol) having a molecular weight of 550, sulfur trioxide pyridine complex (3.8 g, 23.9 mmol), dimethylformamide (total 400 mL), anhydrous THF (total 1000 mL), and triethylamine (total 20 mL) were adjusted.
Nuclear Magnetic Resonance Spectrum with Hydrogen (CDCl$_3$, ppm):
δ 0.8-1.1(b, —NHCH(CH(CH$_3$)CH$_2$CH$_3$)COOCH$_2$CH$_3$),
δ 1.1-1.4(b, —NHCH(CH(CH$_3$)CH$_2$CH$_3$)COOCH$_2$CH$_3$),
δ 1.4-1.8(b, —NHCH(CH(CH$_3$)CH$_2$CH$_3$)COOCH$_2$CH$_3$),
δ 2.67-3.2(b, —NHCH$_2$CH$_2$SO$_4$, —NH(CH$_2$CH$_2$O)$_{11}$CH$_3$),
δ 3.4(s, —NH(CH$_2$CH$_2$O)$_{11}$CH$_3$),
δ 3.4-3.9(b, —NH(CH$_2$CH$_2$O)$_{11}$CH$_3$, —NHCH(CH(CH$_3$)CH$_2$CH$_3$)COOCH$_2$CH$_3$),
δ 3.9-4.3(b, —NHCH(CH(CH$_3$)CH$_2$CH$_3$)COOCH$_2$CH$_3$),
Average molecular weight (M$_w$): 4400

Example 5

Preparation of Poly[(isoleucineethylester)$_{1.21}$(aminomethoxypolyethyleneglycol 550)$_{0.51}$(aminoethylsulfate)$_{0.28}$phosphazene]$_n$ A final product [NP(IleOEt)$_{1.21}$(AMPEG550)$_{0.51}$(AES)$_{0.28}$]$_n$ was obtained in the same manner as in Example 4, except that the amounts of isoleucine ethyl ester hydrochloride (10.22 g, 52.22 mmol), polydichlorophosphazene (5 g, 43.14 mmol), aminoethanol (0.74 g, 12.08 mmol), polyethyleneglycol (12.1 g, 22 mmol) having a molecular weight of 550, sulfur trioxide pyridine complex (4.03 g, 25.29 mmol), dimethylformamide (total 400 mL), anhydrous THF (total 1000 mL), and triethylamine (total 20 mL) were adjusted.
Nuclear Magnetic Resonance Spectrum with Hydrogen (CDCl$_3$, ppm):
δ 0.8-1.1(b, —NHCH(CH(CH$_3$)CH$_2$CH$_3$)COOCH$_2$CH$_3$),
δ 1.1-1.4(b, —NHCH(CH(CH$_3$)CH$_2$CH$_3$)COOCH$_2$CH$_3$),
δ 1.4-1.8(b, —NHCH(CH(CH$_3$)CH$_2$CH$_3$)COOCH$_2$CH$_3$),
δ 2.67-3.2(b, —NHCH$_2$CH$_2$SO$_4$, —NH(CH$_2$CH$_2$O)$_{11}$CH$_3$),
δ 3.4(s, —NH(CH$_2$CH$_2$O)$_{11}$CH$_3$),
δ 3.4-3.9(b, —NH(CH$_2$CH$_2$O)$_{11}$CH$_3$, —NHCH(CH(CH$_3$)CH$_2$CH$_3$)COOCH$_2$CH$_3$),
δ 3.9-4.3(b, —NHCH(CH(CH$_3$)CH$_2$CH$_3$)COOCH$_2$CH$_3$)
Average molecular weight (M$_w$): 2500 ,

Example 6

Preparation of Poly[(isoleucineethylester)$_{1.25}$(aminomethoxypolyethyleneglycol 550)$_{0.45}$(aminoethanol)$_{0.12}$(aminoethylsulfate)$_{0.18}$phosphazene]$_n$ A final product [NP(IleOEt)$_{1.25}$(AMPEG750)$_{0.45}$(Aminoethanol)$_{0.12}$(AES)$_{0.18}$]$_n$ was obtained in the same manner as in Example 4, except that the amounts of isoleucine ethyl ester hydrochloride (10.55 g, 53.93 mmol), polydichlorophosphazene (5 g, 43.14 mmol), aminoethanol (0.79 g, 12.94 mmol), polyethyleneglycol (10.68 g, 19.41 mmol) having a molecular weight of 550, sulfur trioxide pyridine complex (4.29 g, 26.94 mmol), dimethylformamide (total 400 mL), anhydrous THF (total 1000 mL), and triethylamine (total 20 mL) were adjusted.
Nuclear Magnetic Resonance Spectrum with Hydrogen (CDCl$_3$, ppm):
δ 0.8-1.1(b, —NHCH(CH(CH$_3$)CH$_2$CH$_3$)COOCH$_2$CH$_3$),
δ 1.1-1.4(b, —NHCH(CH(CH$_3$)CH$_2$CH$_3$)COOCH$_2$CH$_3$),
δ 1.4-1.8(b, —NHCH(CH(CH$_3$)CH$_2$CH$_3$)COOCH$_2$CH$_3$),
δ 2.67-3.2(b, —NHCH$_2$CH$_2$SO$_4$, —NH(CH$_2$CH$_2$O)$_{11}$CH$_3$),
δ 3.4(s, —NH(CH$_2$CH$_2$O)$_{11}$CH$_3$),
δ 3.4-3.9(b, —NH(CH$_2$CH$_2$O)$_{11}$CH$_3$, —NHCH(CH(CH$_3$)CH$_2$CH$_3$)COOCH$_2$CH$_3$),
δ 3.9-4.3(b, —NHCH(CH(CH$_3$)CH$_2$CH$_3$)COOCH$_2$CH$_3$),
Average molecular weight (M$_w$): 3600

Example 7

Preparation of Poly[(isoleucineethylester)$_{1.38}$(aminomethoxypolyethyleneglycol 750)$_{0.4}$(ethyl-2-(O-glycyl)lactate)$_{0.02}$(aminoethylsulfate)$_{0.2}$phosphazene]$_n$ Dry isoleucine ethyl ester hydrochloride (11.65 g, 59.54 mmol) was dissolved in 200 mL of anhydrous THF including 35 mL of triethylamine. A solution prepared by dissolving polydichlorophosphazene (5 g, 43.14 mmol) in 100 mL of anhydrous THF was added dropwise to the mixed solution in acetone-dry ice bath, and then the temperature was gradually raised to 40° C. to 50° C. and reaction was performed for 24 hours. After cooling the reaction mixture to room temperature, a solution prepared by dissolving dry ethyl-2-(O-glycyl)lactate ammonium oxalate (0.93 g, 4.3 mmol) in 100 mL of anhydrous acetonitrile to which 5 mL of triethylamine was added was gradually added dropwise to the reaction mixture, and then reaction was performed at room temperature for 8 hours.
After cooling the reaction mixture to room temperature, a solution prepared by dissolving dry polyethyleneglycol (12.94 g, 17.26 mmol) having a molecular weight of 750 in 100 mL of anhydrous THF and adding 10 mL of triethylamine thereto was added to the reaction mixture and reaction was performed at a temperature of 40° C. to 50° C. for 24 hours.
The solution in which the reaction was completed was filtered in order to remove produced triethylamine hydrochloride, and the reaction filtrate was concentrated under reduced pressure until a small amount of the solvent remained. The concentrated solution was dissolved in 10 mL of anhydrous THF, and then an excess of hexane was added thereto to induce precipitation. After repeating this process twice or three times, the precipitates were dissolved in a small amount of methanol, placed in MWCO 12000 membrane, dialyzed against methanol at room temperature for 4 days, dialyzed against distilled water for 4 days, and dried at a low temperature to obtain a polyphosphazene polymer [NP(IleOEt)$_{1.38}$(AMPEG750)$_{0.4}$(GlyLacOEt)$_{0.02}$(Aminoethanol)$_{0.2}$]$_n$ including isoleucineethylester, aminomethoxypolyethyleneglycol, ethyl-2-(O-glycyl)lactate, and aminoethanol.

The polyphosphazene polymer [NP(IleOEt)$_{1.38}$(AMPEG750)$_{0.4}$(GlyLacOEt)$_{0.02}$(Aminoethanol)$_{0.2}$]$_n$ obtained in the previous step was dissolved in 200 mL of anhydrous THF and 200 mL of dimethylformamide, and a solution prepared by dissolving sulfur trioxide pyridine complex (3.73 g, 23.46 mmol) in 200 mL of dimethylformamide was added to the reaction solution, and reaction was performed at a temperature of 25° C. to 40° C. for 24 hours. The reaction solution was filtered and the filtrate was concentrated under reduced pressure until a small amount of the solvent remained. The concentrated solution was placed in MWCO 1200 membrane, dialyzed against methanol for 4 days, dialyzed against distilled water for 4 days, and dried at a low temperature to obtain a final product [NP(IleOEt)$_{1.38}$(AMPEG750)$_{0.4}$(GlyLacOEt)$_{0.02}$(AES)$_{0.2}$]$_n$.

Nuclear Magnetic Resonance Spectrum with Hydrogen (CDCl$_3$, ppm):
δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.3-1.5(b, —NHCH$_2$COOCH(C$\underline{H_3}$)COOCH$_2$C$\underline{H_3}$),
δ 1.4-1.8(b, —NHC$\underline{H}$(C$\underline{H}$(CH$_3$)CH$_2$CH$_3$)COOCH$_2$CH$_3$),
δ 1.6-1.7(b, —NHCH$_2$COOCH(C$\underline{H_3}$)COOCH$_2$CH$_3$),
δ 2.67-3.2(b, —NHCH$_2$C$\underline{H_2}$SO$_4$, —NH(CH$_2$CH$_2$O)$_{11}$C$\underline{H_3}$),
δ 3.4(s, —NH(C$\underline{H_2}$CH$_2$O)$_{16}$C$\underline{H_3}$),
δ 3.4-3.9(b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$),
δ 4.0-4.4(b, —NHC$\underline{H_2}$COOCH(CH$_3$)COOC$\underline{H_2}$CH$_3$),
δ 5.2-5.4(b, —NHCH$_2$COOC$\underline{H}$(CH$_3$)COOCH$_2$CH$_3$),
Average molecular weight ($M_w$): 33000

Example 8

Preparation of Poly[(isoleucineethylester)$_{1.23}$(aminomethoxypolyethyleneglycol 550)$_{0.43}$(ethyl-2-(O-glycyl)lactate)$_{0.04}$(aminoethylsulfate)$_{0.3}$phosphazene]$_n$ A final product [NP(IleOEt)$_{1.23}$(AMPEG550)$_{0.43}$(GlyLacOEt)$_{0.04}$(AES)$_{0.3}$]$_n$ was obtained in the same manner as in Example 7, except that polyethyleneglycol having a molecular weight of 550 was used instead of polyethyleneglycol having a molecular weight of 750, and the amounts of isoleucine ethyl ester hydrochloride (10.38 g, 53.07 mmol), polydichlorophosphazene (5 g, 43.14 mmol), ethyl-2-(O-glycyl)lactate ammonium oxalate 1.86 g, 12.6 mmol), aminoethanol (0.79 g, 12.94 mmol), polyethyleneglycol (10.2 g, 18.55 mmol) having a molecular weight of 550, sulfur trioxide pyridine complex (4.5 g, 28.27 mmol), dimethylformamide (total 400 mL), anhydrous acetonitrile (100 mL), anhydrous THF (total 1000 mL), and triethylamine (total 20 mL) were adjusted.

Nuclear Magnetic Resonance Spectrum with Hydrogen (CDCl$_3$, ppm):
δ 0.8-1.1(b, —NHCH(CH(C$\underline{H_3}$)CH$_2$CH$_3$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.3-1.5(b, —NHCH$_2$COOCH(CH$_3$)COOCH$_2$C$\underline{H_3}$),
δ 1.4-1.8(b, —NHC$\underline{H}$(C$\underline{H}$(CH$_3$)CH$_2$CH$_3$)COOCH$_2$CH$_3$),
δ 1.6-1.7(b, —NHCH$_2$COOCH(C$\underline{H_3}$)COOCH$_2$CH$_3$),
δ 2.67-3.2(b, —NHCH$_2$C$\underline{H_2}$SO$_4$, —NH(CH$_2$CH$_2$O)$_{11}$C$\underline{H_3}$),
δ 3.4(s, —NH(CH$_2$CH$_2$O)$_{11}$C$\underline{H_3}$),
δ 3.4-3.9(b, —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$),
δ 4.0-4.4(b, —NHC$\underline{H_2}$COOCH(CH$_3$)COOC$\underline{H_2}$CH$_3$),
δ 5.2-5.4(b, —NHCH$_2$COOC$\underline{H}$(CH$_3$)COOCH$_2$CH$_3$),
Average molecular weight ($M_w$): 34000

Example 9

Preparation of Poly[(isoleucineethylester)$_{1.38}$(aminomethoxypolyethyleneglycol 750)$_{0.32}$(aminoethylsulfate)$_{0.15}$(aminoethylsuccinate)$_{0.15}$phosphazene]$_n$ Dry isoleucine ethyl ester hydrochloride (11.65 g, 59.53 mmol) was dissolved in 200 mL of anhydrous THF including 35 mL of triethylamine. A solution prepared by dissolving polydichlorophosphazene (5 g, 43.14 mmol) in 100 mL of anhydrous THF was added dropwise to the mixed solution in acetone-dry ice bath, and then the temperature was gradually raised to 40° C. to 50° C. and reaction was performed for 24 hours. After cooling the reaction mixture to room temperature, a solution prepared by dissolving dry aminoethanol (0.94 g, 15.53 mmol) in 100 mL of anhydrous THF and adding 5 mL of triethylamine thereto was added to the reaction mixture, and then reaction was performed at a temperature of 40° C. to 50° C. for 24 hours.

After cooling the reaction mixture to room temperature, a solution prepared by dissolving dry polyethyleneglycol (8.41 g, 11.21 mmol) having a molecular weight of 750 in 200 mL of anhydrous THF and adding 5 mL of triethylamine was added to the reaction mixture and reaction was performed at a temperature of 40° C. to 50° C. for 24 hours.

The solution in which the reaction was completed was filtered in order to remove produced triethylamine hydrochloride, and the reaction filtrate was concentrated under reduced pressure until a small amount of the solvent remained. The concentrated solution was dissolved in 10 mL of anhydrous THF, and then an excess of hexane was added thereto to induce precipitation. After repeating this process twice or three times, the precipitates were dissolved in a small amount of methanol, placed in MWCO 12000 membrane, dialyzed against methanol at room temperature for 4 days, dialyzed against distilled water for 4 days, and dried at a low temperature to obtain a polyphosphazene polymer [NP(IleOEt)$_{1.38}$(AMPEG750)$_{0.32}$(Aminoethanol)$_{0.3}$]$_n$ including isoleucineethylester, aminomethoxypolyethyleneglycol, and aminoethanol.

The polyphosphazene polymer [NP(IleOEt)$_{1.38}$(AMPEG750)$_{0.32}$(Aminoethanol)$_{0.3}$]$_n$ obtained in the previous step was dissolved in 200 mL of anhydrous THF and 200 mL of dimethylformamide, and a solution prepared by dissolving 1 equivalent of sulfur trioxide pyridine complex (1.4 g, 8.78 mmol) in 200 mL of dimethylformamide was added to the reaction solution, and reaction was performed at a temperature of 25° C. to 40° C. for 24 hours. After cooling the reaction solution to room temperature, 2 equivalents of anhydrous succinic acid (1.76 g, 17.57 mmol) and 2 equivalents of dimethylaminopyridine (2.15 g, 17.57 mmol) were added to the reaction mixture, and then reaction was further performed at a temperature of 25° C. to 40° C. for 24 hours. The reaction solution was filtered and the filtrate was concentrated under reduced pressure until a small amount of the solvent remained, and the concentrated solution was placed in MWCO 1200 membrane, dialyzed against methanol for 4 days, dialyzed against distilled water for 4 days, and dried at a low temperature to obtain a final product [NP(IleOEt)$_{1.38}$(AMPEG750)$_{0.32}$(AES)$_{0.15}$(Aminoethylsuccinate)$_{0.15}$]$_n$.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.4-1.8(b, —NHC$\underline{H}$(CH(CH$_3$)CH$_2$CH$_3$)COOC$\underline{H_2}$CH$_3$),
δ 2.5-2.7(b, —NHC$\underline{H_2}$CH$_2$OCOC$\underline{H_2}$CH$_2$COOH),
δ 2.67-3.2(b, —NHCH$_2$C$\underline{H_2}$SO$_4$, —NH(CH$_2$CH$_2$O)$_{16}$C$\underline{H_3}$),
δ 2.9-3.2(b, —NHCH$_2$CH$_2$OCOCH$_2$C$\underline{H_2}$COOH),
δ 3.4(s, —NH(CH$_2$CH$_2$O)$_{16}$C$\underline{H_3}$),
δ 3.4-3.9(b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$, —NHCH$_2$C$\underline{H_2}$OCOCH$_2$CH$_2$COOH), Average molecular weight (M$_w$): 2200

Example 10

Preparation of Poly[(isoleucineethylester)$_{1.22}$(aminomethoxypolyethyleneglycol 550)$_{0.5}$(aminoethylsulfate)$_{0.1}$(aminoethylsuccinate)$_{0.18}$phosphazene]$_n$ A final product [NP(IleOEt)$_{1.22}$(AMPEG750)$_{0.5}$(AES)$_{0.1}$(Aminoethylsuccinate)$_{0.18}$]$_n$ was obtained in the same manner as in Example 9, except that polyethyleneglycol having a molecular weight of 550 was used instead of polyethyleneglycol having a molecular weight of 750, and the amounts of isoleucine ethyl ester hydrochloride (10.30 g, 52.64 mmol), polydichlorophosphazene (5 g, 43.14 mmol), aminoethanol (0.79 g, 12.94 mmol), polyethyleneglycol (11.86 g, 21.58 mmol) having a molecular weight of 550, sulfur trioxide pyridine complex (1.38 g, 8.67 mmol), dimethylformamide (total 400 mL), 2 equivalents of anhydrous succinic acid (1.72 g, 17.18 mmol), 2 equivalents of dimethylaminopyridine (2.1 g, 17.18 mmol), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.4-1.8(b, —NHC$\underline{H}$(CH(CH$_3$)CH$_2$CH$_3$)COOC$\underline{H_2}$CH$_3$),
δ 2.5-2.7(b, —NHC$\underline{H_2}$CH$_2$OCOC$\underline{H_2}$CH$_2$COOH),
δ 2.67-3.2(b, —NHCH$_2$C$\underline{H_2}$SO$_4$, —NH(CH$_2$CH$_2$O)$_{16}$C$\underline{H_3}$),
δ 2.9-3.2(b, —NHCH$_2$CH$_2$OCOCH$_2$C$\underline{H_2}$COOH),
δ 3.4(s, —NH(CH$_2$CH$_2$O)$_{11}$C$\underline{H_3}$),
δ 3.4-3.9(b, —NH(C$\underline{H_2}$C$\underline{H_2}$O)$_{11}$CH$_3$, —NHCH(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$, —NHCH$_2$C$\underline{H_2}$OCOCH$_2$CH$_2$COOH), Average molecular weight (M$_w$): 3500

Example 11

Preparation of Poly[(isoleucineethylester)$_{1.39}$(aminomethoxypolyethyleneglycol 750)$_{0.31}$(aminoethylsulfate)$_{0.13}$(aminoethylglutarate)$_{0.17}$phosphazene]$_n$ A final product [NP(IleOEt)$_{1.39}$(AMPEG750)$_{0.31}$(AES)$_{0.13}$(AminoethylGlutarate)$_{0.17}$]$_n$ was obtained in the same manner as in Example 9, except that anhydrous glutaric acid was used instead of anhydrous succinic acid, and the amounts of isoleucine ethyl ester hydrochloride (11.74 g, 59.98 mmol), polydichlorophosphazene (5 g, 43.14 mmol), aminoethanol (0.79 g, 12.94 mmol), polyethyleneglycol (10.03 g, 13.37 mmol) having a molecular weight of 750, sulfur trioxide pyridine complex (1.42 g, 8.91 mmol), dimethylformamide (total 400 mL), 2 equivalents of anhydrous glutaric acid (3.65 g, 32.01 mmol), 2 equivalents of dimethylaminopyridine (3.91 g, 32.01 mmol), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.4-1.8(b, —NHC$\underline{H}$(CH(CH$_3$)CH$_2$CH$_3$)COOCH$_2$CH$_3$),
δ 2.1-2.32(b, —NHCH$_2$C$\underline{H_2}$OCOC$\underline{H_2}$CH$_2$CH$_2$COOH),
δ 2.67-3.2(b, —NHCH$_2$C$\underline{H_2}$SO$_4$, —NH(CH$_2$CH$_2$O)$_{16}$C$\underline{H_3}$),
δ 2.9-3.2(b, —NHCH$_2$CH$_2$OCOCH$_2$CH$_2$C$\underline{H_2}$COOH),
δ 3.4(s, —NH(CH$_2$CH$_2$O)$_{16}$C$\underline{H_3}$),
δ 3.4-3.9(b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH), Average molecular weight (M$_w$): 4500

Example 12

Preparation of Poly[(isoleucineethylester)$_{1.21}$(aminomethoxypolyethyleneglycol 550)$_{0.49}$(aminoethylsulfate)$_{0.2}$(aminoethylglutarate)$_{0.1}$phosphazene]$_n$ A final product [NP(IleOEt)$_{1.21}$(AMPEG550)$_{0.49}$(AES)$_{0.2}$(AminoethylGlutarate)$_{0.1}$]$_n$ was obtained in the same manner as in Example 11, except that polyethyleneglycol having a molecular weight of 550 was used instead of polyethyleneglycol having a molecular weight of 750, and the amounts of isoleucine ethyl ester hydrochloride (10.22 g, 52.2 mmol), polydichlorophosphazene (5 g, 43.14 mmol), aminoethanol (0.79 g, 12.94 mmol), polyethyleneglycol (11.63 g, 21.14 mmol) having a molecular weight of 550, sulfur trioxide pyridine complex (1.12 g, 11.14 mmol), dimethylformamide (total 400 mL), 2 equivalents of anhydrous glutaric acid (3.59 g, 31.5 mmol), 2 equivalents of dimethylaminopyridine (3.85 g, 31.49 mmol), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(CH$_3$)C$\underline{H_2}$CH$_3$)COOCH$_2$CH$_3$),
δ 1.1-1.4(b, —NHCH(CH(CH$_3$)C$\underline{H_2}$CH$_3$)COOCH$_2$C$\underline{H_3}$),
δ 1.4-1.8(b, —NHC$\underline{H}$(CH(CH$_3$)CH$_2$CH$_3$)COOCH$_2$CH$_3$),
δ 2.1-2.32(b, —NHCH$_2$C$\underline{H_2}$OCOC$\underline{H_2}$CH$_2$CH$_2$COOH),
δ 2.67-3.2(b, —NHCH$_2$C$\underline{H_2}$SO$_4$, —NH(CH$_2$CH$_2$O)$_{16}$C$\underline{H_3}$),
δ 2.9-3.2(b, —NHCH$_2$CH$_2$OCOCH$_2$CH$_2$C$\underline{H_2}$COOH),
δ 3.4(s, —NH(CH$_2$CH$_2$O)$_{11}$C$\underline{H_3}$),
δ 3.4-3.9(b, —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH), Average molecular weight (M$_w$): 4600

Example 13

Preparation of Poly[(isoleucineethylester)$_{1.36}$(aminomethoxypolyethyleneglycol 750)$_{0.28}$(aminoethylsulfate)$_{0.21}$(aminoethyladipate)$_{0.15}$phosphazene]$_n$ A final product [NP(IleOEt)$_{1.36}$(AMPEG750)$_{0.28}$(AES)$_{0.21}$(AminoethylAdipate)$_{0.15}$]$_n$ was obtained in the same manner as in Example 9, except that anhydrous adipic acid was used instead of anhydrous succinic acid, and the amounts of isoleucine ethyl ester hydrochloride (11.48 g, 59.67 mmol), polydichlorophosphazene (5 g, 43.14 mmol), aminoethanol (0.79 g, 12.94 mmol), polyethyleneglycol (9.06 g, 12.08 mmol) having a molecular weight of 750, sulfur trioxide pyridine complex (1.48 g, 9.32 mmol), dimethylformamide (total 400 mL), 2 equivalents of anhydrous adipic acid (2.63 g, 20.54 mmol), 2 equivalents of dimethylaminopyridine (2.51 g, 20.54 mmol), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOC$\underline{H_2}$C$\underline{H_3}$),
δ 1.4-1.8(b, —NHC$\underline{H}$(C$\underline{H}$(CH$_3$)CH$_2$CH$_3$)COOCH$_2$CH$_3$),
δ 1.52-1.64(b, —NHCH$_2$CH$_2$OCOC$\underline{H_2}$C$\underline{H_2}$CH$_2$CH$_2$COOH),
δ 2.3-2.32(b, —NHCH$_2$CH$_2$OCOCH$_2$CH$_2$CH$_2$C$\underline{H_2}$COOH),
δ 2.67-3.2(b, —NHCH$_2$C$\underline{H_2}$SO$_4$, —NH(CH$_2$CH$_2$O)$_{16}$C$\underline{H_3}$),
δ 3.4(s, —NH(CH$_2$CH$_2$O)$_{16}$C$\underline{H_3}$),
δ 3.4-3.9(b, —NH(C$\underline{H_2}$C$\underline{H_2}$O)$_{16}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
Average molecular weight (M$_w$): 3700

Example 14

Preparation of Poly[(isoleucineethylester)$_{1.21}$(aminomethoxypolyethyleneglycol 550)$_{0.49}$(aminoethylsulfate)$_{0.12}$(aminoethyladipate)$_{0.18}$phosphazene]$_n$ A final product [NP(IleOEt)$_{1.21}$(AMPEG550)$_{0.49}$(AES)$_{0.12}$(AminoethylAdipate)$_{0.18}$]$_n$ was obtained in the same manner as in Example 13, except that polyethyleneglycol having a molecular weight of 550 was used instead of polyethyleneglycol having a molecular weight of 750, and the amounts of isoleucine ethyl ester hydrochloride (10.22 g, 52.2 mmol), polydichlorophosphazene (5 g, 43.14 mmol), aminoethanol (0.79 g, 12.94 mmol), polyethyleneglycol (11.63 g, 21.14 mmol) having a molecular weight of 550, sulfur trioxide pyridine complex (1.35 g, 11.02 mmol), dimethylformamide (total 400 mL), 2 equivalents of anhydrous adipic acid (3.14 g, 24.52 mmol), 2 equivalents of dimethylaminopyridine (3 g, 24.52 mmol), anhydrous THF (total 1000 mL), and triethylamine (total 20 mL) were adjusted.

Nuclear Magnetic Resonance Spectrum with Hydrogen (CDCl$_3$, ppm):

δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOC$\underline{H_2}$C$\underline{H_3}$),
δ 1.4-1.8(b, —NHC$\underline{H}$(C$\underline{H}$(CH$_3$)CH$_2$CH$_3$)COOCH$_2$CH$_3$),
δ 1.52-1.64(b, —NHCH$_2$CH$_2$OCOC$\underline{H_2}$C$\underline{H_2}$CH$_2$CH$_2$COOH),
δ 2.3-2.32(b, —NHCH$_2$CH$_2$OCOCH$_2$CH$_2$CH$_2$C$\underline{H_2}$COOH),
δ 2.67-3.2(b, —NHCH$_2$C$\underline{H_2}$SO$_4$, —NH(CH$_2$CH$_2$O)$_{16}$C$\underline{H_3}$),
δ 3.4(s, —NH(CH$_2$CH$_2$O)$_{11}$C$\underline{H_3}$),
δ 3.4-3.9(b, —NH(C$\underline{H_2}$C$\underline{H_2}$O)$_{11}$CH$_3$, —NHC$\underline{H}$(CH(CH$_3$)CH$_2$CH$_3$)COOCH$_2$CH$_3$),
δ 3.9-4.3(b, —NHCH(CH(CH$_3$)CH$_2$CH$_3$)COOC$\underline{H_2}$CH$_3$, —NHCH$_2$C$\underline{H_2}$OCOCH$_2$CH$_2$CH$_2$COOH),
Average molecular weight (M$_w$): 2900

Example 15

Preparation of Poly[(isoleucineethylester)$_{1.4}$(aminomethoxypolyethyleneglycol 750)$_{0.3}$(aminoethylsulfate)$_{0.16}$(aminoethylsuccinatepolyethyleneimine)$_{0.14}$phosphazene]$_n$

[NP(IleOEt)$_{1.4}$(AMPEG750)$_{0.3}$(AES)$_{0.16}$(Aminoethylsuccinate)$_{0.14}$]$_n$ was obtained in the same manner as in Example 9 using isoleucine ethyl ester hydrochloride (11.82 g, 60.4 mmol), polydichlorophosphazene (5 g, 43.14 mmol), aminoethanol (0.79 g, 12.94 mmol), polyethyleneglycol (9.71 g, 12.94 mmol) having a molecular weight of 750, sulfur trioxide pyridine complex (1.43 g, 8.98 mmol), dimethylformamide (total 400 mL), 2 equivalents of anhydrous succinic acid (1.8 g, 18 mmol), 2 equivalents of dimethylaminopyridine (2.2 g, 18 mmol), anhydrous THF (total 1000 mL), and triethylamine (total 20 mL).

The obtained [NP(IleOEt)$_{1.4}$(AMPEG750)$_{0.3}$(AES)$_{0.16}$(Aminoethylsuccinate)$_{0.14}$]$_n$ was dissolved in 200 mL of chloroform, and isobutylchloroformate (0.25 g) and triethylamine (5 mL) were added thereto, followed by activation for 40 minutes. Then, polyethyleneimine (PEI, 16.2 g, 9 mmol) having a molecular weight of 1800 dissolved in chloroform was added to the solution and reaction was performed. After 18 hours, the reaction mixture was concentrated under reduced pressure, precipitated using a KF solution, dialyzed against distilled water at 4° C. for 3 days, and dried at a low temperature to obtain a final product [NP(IleOEt)$_{1.4}$(AMPEG750)$_{0.3}$(AES)$_{0.16}$(AminoethylsuccinatePEI)$_{0.14}$]$_n$.

Nuclear Magnetic Resonance Spectrum with Hydrogen (CDCl$_3$, ppm):

δ 0.7-1.1(b, —NHCH(CH(C$\underline{H_3}$)CH$_2$C$\underline{H_3}$)COOCH$_2$CH$_3$),
δ 1.1-1.3(b, —NHCH(CH(CH$_3$)C$\underline{H_2}$CH$_3$)COOC$\underline{H_2}$C$\underline{H_3}$),
δ 1.4-1.8(b, —NHC$\underline{H}$(C$\underline{H}$(CH$_3$)CH$_2$CH$_3$)COOCH$_2$CH$_3$, —NHCH$_2$CH$_2$OCOC$\underline{H_2}$CH$_2$CONH-PEI),
δ 2.5-2.7(b, —NHCH$_2$CH$_2$OCOC$\underline{H_2}$CH$_2$CONH-PEI),
δ 2.67-3.2(b, —NHCH$_2$C$\underline{H_2}$SO$_4$,
δ 3.4(s, —NH(CH$_2$CH$_2$O)$_{16}$C$\underline{H_3}$),
δ 3.4-3.8(b, —NH(C$\underline{H_2}$C$\underline{H_2}$O)$_{16}$CH$_3$), —NHCH$_2$CH$_2$OCOC$\underline{H_2}$CH$_2$CONH-PEI),
δ 3.9-4.3(b, —NHCH(CH(CH$_3$)CH$_2$CH$_3$)COOC$\underline{H_2}$CH$_3$),
Average molecular weight (M$_w$): 3400

Example 16

Preparation of Poly[(isoleucineethylester)$_{1.41}$(aminomethoxypolyethyleneglycol 750)$_{0.4}$(aminoethylsulfate)$_{0.12}$(aminoethylsuccinateimidazole)$_{0.07}$phosphazene]$_n$

[NP(IleOEt)$_{1.41}$(AMPEG750)$_{0.4}$(AES)$_{0.12}$(Aminoethylsuccinate)$_{0.07}$]$_n$ was obtained in the same manner as in Example 9 using isoleucine ethyl ester hydrochloride (11.9 g, 60.83 mmol), polydichlorophosphazene (5 g, 43.14 mmol), aminoethanol (0.5 g, 8.2 mmol), polyethyleneglycol (12.94 g, 17.26 mmol) having a molecular weight of 750, sulfur trioxide pyridine complex (1.24 g, 7.82 mmol), dimethylformamide (total 400 mL), 2 equivalents of anhydrous succinic acid (1.57 g, 15.73 mmol), 2 equivalents of dimethylaminopyridine (1.92 g, 15.73 mmol), anhydrous THF (total 1000 mL), and triethylamine (total 20 mL).

The obtained [NP(IleOEt)$_{1.41}$(AMPEG750)$_{0.4}$(AES)$_{0.12}$(Aminoethylsuccinate)$_{0.07}$]$_n$ was dissolved in 400 mL of THF. Each of the solutions respectively prepared by dissolving 10 equivalents of diisopropylcarbodiimide (4.38 g) and 10 equivalents of n-hydroxysuccinimide (4 g) in 50 mL of THF was added to the polymer solution, followed by activation for 40 minutes. Then, a solution prepared by dissolving 5 equivalents of 1-(3-aminopropylimidazole) (2.18 g) in THF was added thereto, reaction was performed in an ice bath for 5 hours and then at room temperature for hours to obtain a final product [NP(IleOEt)$_{1.41}$(AMPEG750)$_{0.4}$(AES)$_{0.12}$(AminoethylsuccinateImidazole)$_{0.7}$]$_n$.

Nuclear Magnetic Resonance Spectrum with Hydrogen (CDCl$_3$, ppm):
δ 0.7-1.1(b, —NHCH(CH(C$\underline{H_3}$)CH$_2$C$\underline{H_3}$)COOCH$_2$CH$_3$),
δ 1.1-1.3(b, —NHCH(CH(CH$_3$)C$\underline{H_2}$CH$_3$)COOC$\underline{H_2}$CH$_3$),
δ 1.4-1.8(b, —NHC$\underline{H}$(C$\underline{H}$(CH$_3$)CH$_2$CH$_3$)COOCH$_2$CH$_3$),
δ 2.5-2.7(b, —NHCH$_2$CH$_2$OCOC$\underline{H_2}$CH$_2$CONH-Imi),
δ 2.67-3.2(b, —NHCH$_2$C$\underline{H_2}$SO$_4$),
δ 3.4(s, —NH(CH$_2$CH$_2$O)$_{16}$C$\underline{H_3}$),
δ 3.4-3.8(b, —NH(C$\underline{H_2}$C$\underline{H_2}$O)$_{16}$CH$_3$), —NHCH$_2$CH$_2$OCOC$\underline{H_2}$CH$_2$CONH-Imi)
δ 3.9-4.3(b, —NHCH(CH(CH$_3$)CH$_2$CH$_3$)COOC$\underline{H_2}$CH$_3$)
δ 6.8-7.8(b, —NHCH$_2$CH$_2$OCOC$\underline{H_2}$CH$_2$CONH-Imi)
Average molecular weight (M$_w$): 4500

Example 17

Preparation of Poly[(isoleucineethylester)$_{1.49}$(aminomethoxypolyethyleneglycol 750)$_{0.34}$(aminoethylsulfate)$_{0.10}$(aminoethylsuccinatepolypeptide)$_{0.07}$phosphazene]$_n$

[NP(IleOEt)$_{1.49}$(AMPEG750)$_{0.34}$(AES)$_{0.1}$(Aminoethylsuccinate)$_{0.07}$]$_n$ was obtained in the same manner as in Example 9 using isoleucine ethyl ester hydrochloride (12.58 g, 64.28 mmol), polydichlorophosphazene (5 g, 43.14 mmol), aminoethanol (0.26 g, 4.31 mmol), polyethyleneglycol (11 g, 14.67 mmol) having a molecular weight of 750, sulfur trioxide pyridine complex (1.32 g, 8.3 mmol), dimethylformamide (total 400 mL), anhydrous succinic acid (0.83 g, 8.3 mmol), dimethylaminopyridine (1.02 g, 8.3 mmol), anhydrous THF (total 1000 mL), and triethylamine (total 20 mL).

A solution of 5 equivalents of hexylamine (0.29 g, 2.84 mmol) and 1 equivalent of polypeptide (amino acid sequence: CRRRRHHHHHGGGGGRGDS, 1.29 g, 0.57 mmol) was added to a flask in which 5 g of the polymer obtained as described above was dissolved in 400 mL of dimethyl sulfoxide, and reaction was performed at room temperature for 24 hours. Then, the resultant was dialyzed against distilled water at 4° C. for 3 days, and dried at a low temperature to obtain a final product [NP(IleOEt)$_{1.49}$(AMPEG750)$_{0.34}$(AES)$_{0.1}$(AminoethylsuccinateCRRRRHHHHHHGGG GGRGDS)$_{0.07}$]$_n$.

Nuclear Magnetic Resonance Spectrum with Hydrogen (CDCl3, ppm):
δ 0.7-1.1(b, —NHCH(CH(CH$_3$)CH$_2$CH$_3$)COOCH$_2$CH$_3$),
δ 1.1-1.3(b, —NHCH(CH(CH$_3$)CH$_2$CH$_3$)COOCH$_2$CH$_3$),
δ 1.4-1.8(b, —NHCH(CH(CH$_3$)CH$_2$CH$_3$)COOCH$_2$CH$_3$, —NHCH$_2$CH$_2$OCOCH$_2$CH$_2$CONH-PEI),
δ 2.5-2.7(b, —NHCH$_2$CH$_2$OCOCH$_2$CH$_2$CONH-PEI),
δ 2.67-3.2(b, —NHCH$_2$CH$_2$SO$_4$),
δ 3.4(s, —NH(CH$_2$CH$_2$O)$_{16}$CH$_3$),
δ 3.4-3.8(b, —NH(CH$_2$CH$_2$O)$_{16}$CH$_3$), —NHCH$_2$CH$_2$OCOCH$_2$CH$_2$CONH-PEI),
δ 3.9-4.3(b, —NHCH(CH(CH$_3$)CH$_2$CH$_3$)COOCH$_2$CH$_3$),
δ 8.73(b, CHNCHNHCH, imidazole),
Average molecular weight (Mw): 1840

Example 18

Preparation of Poly[(isoleucineethylester)$_{1.40}$(aminomethoxypolyethyleneglycol 750)$_{0.30}$(aminoethylmethacrylateethylsulfate)$_{0.16}$(aminoethylmethacrylate)$_{0.14}$phosphazene]$_n$ Dry isoleucine ethyl ester hydrochloride (9.79 g, 50.04 mmol) was dissolved in 500 mL of anhydrous tetrahydrofuran including 30 mL of triethylamine. A solution prepared by dissolving poly(dichlorophosphazene) (5.00 g, 43.14 mmol) in 100 mL of tetrahydrofuran was added dropwise to the mixed solution in an acetone-dry ice bath, and then the temperature was gradually raised to 40° C. to 50° C. and reaction was performed for 24 hours. After cooling the reaction mixture to room temperature, a solution prepared by dissolving dry aminomethacrylate hydrochloride (3.58 g, 21.57 mmol) in 100 mL of dimethylformamide was added to a reaction mixture, and reaction was performed at 40° C. to 50° C. for 24 hours. After cooling the reaction mixture to room temperature again, a solution prepared by dissolving dry polyethyleneglycol (8.07 g, 14.67 mmol) having a molecular weight of 750 in 200 mL of anhydrous tetrahydrofuran and adding 5 mL of triethylamine thereto was added to the reaction mixture, and reaction was performed at a temperature of 40° C. to 50° C. for 24 hours.

The reaction solution was filtered to remove produced triethylamine hydrochloride and the filtrate was concentrated under reduced pressure until a small amount of the solvent remained. The concentrated solution was dissolved in 10 mL of tetrahydrofuran, and an excess of hexane was added thereto to induce precipitation. After repeating this process twice or three times, the precipitates were dissolved in a small amount of methanol, placed in MWCO 1200 membrane (Spectrum Laboratories, Inc.), dialyzed against methanol at room temperature for 5 days, dialyzed against distilled water for 5 days, and dried at a low temperature to obtain a poly(dichlorophosphazene) polymer [NP(IleOEt)$_{1.40}$(AMPEG750)$_{0.30}$(AEMA)$_{0.30}$]$_n$.

Then, a solution prepared by dissolving sulfur trioxide pyridine complex (1.32 g, 8.3 mmol) in dimethylformamide (total 400 mL) was added dropwise to the reaction mixture, and reaction was performed at a temperature of 40° C. to 50° C. for 24 hours to obtain 9.5 g of [NP(IleOEt)$_{1.40}$(AMPEG750)$_{0.30}$(AEMAES)$_{0.16}$(AEMA)$_{0.14}$]$_n$ (yield: 82%).

Nuclear Magnetic Resonance Spectrum with Hydrogen (CDCl$_3$, ppm):
δ 0.8-1.1(b, —NHCH(CH(C$\underline{H_3}$)CH$_2$C$\underline{H_3}$)COOCH$_2$CH$_3$),
δ 1.1-1.4(b, —NHCH(CH(CH$_3$)C$\underline{H_2}$CH$_3$)COOC$\underline{H_2}$C$\underline{H_3}$),
δ 1.4 to 1.8(b, —NHC$\underline{H}$(C$\underline{H}$(CH$_3$)CH$_2$CH$_3$)COOCH$_2$CH$_3$),
δ 1.9(s, —NHCH$_2$CH$_2$O$_2$C(C$\underline{H_3}$)C=CH$_2$),
δ 2.67-3.2(b, —NHCH$_2$CH$_2$O$_2$C(C$\underline{H_3}$)CCHC$\underline{H_2}$SO$_4$,)
δ 3.4(s, —NH(CH$_2$CH$_2$O)$_{11}$C$\underline{H_3}$), δ 3.4-3.9(b, —NH(C̲H̲₂C̲H̲₂O)₁₁CH₃, —NH C̲H̲(CH(CH₃)CH₂CH₃)COOCH₂CH₃),
δ 3.9 to 4.3(b, —NHCH(CH(CH₃)CH₂CH₃)COO C̲H̲₂CH₃),
δ 5.5(s, —NHCH₂CH₂O₂C(CH₃)C=C̲H̲₂),
δ 6.1(s, —NHCH₂CH₂O₂C(CH₃)C=C̲H̲₂),
Average molecular weight ($M_w$): 41000

Comparative Example 1

Preparation of Poly[(isoleucineethylester)$_{1.26}$(aminomethoxypolyethyleneglycol 750)$_{0.44}$(aminoethanol)$_{0.36}$phosphazene]$_n$ A final product [NP(IleOEt)$_{1.26}$(AMPEG750)$_{0.44}$(Aminoethanol)$_{0.36}$]$_n$ was obtained in the same manner as in Example 1, except that isoleucine ethyl ester hydrochloride (10.64 g, 54.36 mmol), polydichlorophosphazene (5 g, 43.14 mmol), aminoethanol (0.79 g, 12.94 mmol), polyethyleneglycol (14.24 g, 18.98 mmol) having a molecular weight of 750, anhydrous THF (total 1000 mL), and triethylamine (total 20 mL) were used without perform the reaction with sulfur trioxide pyridine complex.

Nuclear Magnetic Resonance Spectrum with Hydrogen (CDCl₃, ppm):
δ 0.8-1.1(b, —NHCH(CH(C̲H̲₃)CH₂CH₃)COOCH₂CH₃),
δ 1.1-1.4(b, —NHCH(CH(CH₃)C̲H̲₂CH₃)COOCH₂C̲H̲₃),
δ 1.4-1.8(b, —NHC̲H̲(CH(CH₃)CH₂CH₃)COOCH₂CH₃),
δ 2.67-3.2(b, —NHCH₂C̲H̲₂OH, —NH(CH₂CH₂O)₁₆ C̲H̲₃),
δ 2.9-3.2(b, —NHCH₂CH₂OCOCH₂C̲H̲₂COOH),
δ 3.4(s, —NH(CH₂CH₂O)₁₆C̲H̲₃),
δ 3.4-3.9(b, —NH(C̲H̲₂C̲H̲₂O)₁₆CH₃, —NH C̲H̲(CH(CH₃)CH₂CH₃)COOCH₂CH₃),
δ 3.9-4.3(b, —NHCH(CH(CH₃)CH₂CH₃)COOC̲H̲₂CH₃),
Average molecular weight ($M_w$): 6800

Comparative Example 2

Preparation of Poly[(isoleucineethylester)$_{1.38}$(aminomethoxypolyethyleneglycol 750)$_{0.32}$(aminoethylsuccinate)$_{0.15}$phosphazene]$_n$ A final product [NP(IleOEt)$_{1.32}$(AMPEG750)$_{0.31}$(Aminoethylsuccinate)$_{0.36}$]$_n$ was obtained in the same manner as in Example 9, except that isoleucine ethyl ester hydrochloride (11.14 g, 56.95 mmol), polydichlorophosphazene (5 g, 43.14 mmol), aminoethanol (0.95 g, 15.53 mmol), polyethyleneglycol (10.35 g, 13.8 mmol) having a molecular weight of 750, anhydrous succinic acid (1.16 g, 11.64 mmol), dimethylaminopyridine (1.42 g, 11.64 mmol), anhydrous THF (total 1000 mL), and triethylamine (total 20 mL) were used.

Nuclear Magnetic Resonance Spectrum with Hydrogen (CDCl₃, ppm):
δ 0.8-1.1(b, —NHCH(CH(C̲H̲₃)CH₂CH₃)COOCH₂CH₃),
δ 1.1-1.4(b, —NHCH(CH(CH₃)C̲H̲₂CH₃)COOCH₂C̲H̲₃),
δ 1.4-1.8(b, —NHC̲H̲(CH(CH₃)CH₂CH₃)COOCH₂CH₃),
δ 2.5-2.7(b, —NHCH₂CH₂OCOC̲H̲₂CH₂COOH),
δ 2.67-3.2(b, —NHCH₂C̲H̲₂OH, —NH(CH₂CH₂O)₁₆ C̲H̲₃),
δ 2.9-3.2(b, —NHCH₂CH₂OCOCH₂C̲H̲₂COOH),
δ 3.4(s, —NH(CH₂CH₂O)₁₆C̲H̲₃),
δ 3.4-3.9(b, —NH(C̲H̲₂C̲H̲₂O)₁₆CH₃, —NH C̲H̲(CH(CH₃)CH₂CH₃)COOCH₂CH₃),
δ 3.9-4.3(b, —NHCH(CH(CH₃)CH₂CH₃)COOC̲H̲₂CH₃, —NHCH₂C̲H̲₂OCOCH₂CH₂COOH),
Average molecular weight ($M_w$): 4400

Comparative Example 3

Preparation of Poly[(isoleucineethylester)$_{1.48}$(aminomethoxypolyethyleneglycol 750)$_{0.41}$(aminoethylglutarate)$_{0.11}$phosphazene]$_n$ A final product [NP(IleOEt)$_{1.48}$(AMPEG750)$_{0.41}$(AminoethylGlutarate)$_{0.11}$]$_n$ was obtained in the same manner as in Example 9, except that isoleucine ethyl ester hydrochloride (12.5 g, 63.85 mmol), polydichlorophosphazene (5 g, 43.14 mmol), aminoethanol (0.29 g, 4.7 mmol), polyethyleneglycol (13.27 g, 17.68 mmol) having a molecular weight of 750, anhydrous glutaric acid (3.17 g, 27.81 mmol), dimethylaminopyridine (3.4 g, 27.81 mmol), anhydrous THF (total 1000 mL), and triethylamine (total 20 mL) were used.

Nuclear Magnetic Resonance Spectrum with Hydrogen (CDCl₃, ppm):
δ 0.8-1.1(b, —NHCH(CH(C̲H̲₃)CH₂CH₃)COOCH₂CH₃),
δ 1.1-1.4(b, —NHCH(CH(CH₃)C̲H̲₂CH₃)COOCH₂C̲H̲₃),
δ 1.4-1.8(b, —NHC̲H̲(CH(CH₃)CH₂CH₃)COOCH₂CH₃),
δ 2.1-2.32(b, —NHCH₂CH₂OCOC̲H̲₂CH₂CH₂COOH),
δ 2.67-3.2(b, —NHCH₂C̲H̲₂OH, —NH(CH₂CH₂O)₁₆ C̲H̲₃),
δ 2.9-3.2(b, —NHCH₂CH₂OCOCH₂CH₂C̲H̲₂COOH),
δ 3.4(s, —NH(CH₂CH₂O)₁₆C̲H̲₃),
δ 3.4-3.9(b, —NH(C̲H̲₂C̲H̲₂O)₁₆CH₃, —NH C̲H̲(CH(CH₃)CH₂CH₃)COOCH₂CH₃),
δ 3.9-4.3(b, —NHCH(CH(CH₃)CH₂CH₃)COOC̲H̲₂CH₃, —NHCH₂C̲H̲₂OCOCH₂CH₂CH₂COOH),
Average molecular weight ($M_w$): 5600

Comparative Example 4

Preparation of Poly[(isoleucineethylester)$_{1.44}$(aminomethoxypolyethyleneglycol 750)$_{0.34}$(aminoethyladipate)$_{0.23}$phosphazene]$_n$ A final product [NP(IleOEt)$_{1.44}$(AMPEG750)$_{0.34}$(AminoethylAdipate)$_{0.23}$]$_n$ was obtained in the same manner as in Example 9, except that isoleucine ethyl ester hydrochloride (12.16 g, 62.13 mmol), polydichlorophosphazene (5 g, 43.14 mmol), aminoethanol (0.61 g, 9.92 mmol), polyethyleneglycol (11 g, 14.67 mmol) having a molecular weight of 750, anhydrous adipic acid (2.91 g, 22.71 mmol), dimethylaminopyridine (2.77 g, 22.71 mmol), anhydrous THF (total 1000 mL), and triethylamine (total 20 mL) were used.

Nuclear Magnetic Resonance Spectrum with Hydrogen (CDCl₃, ppm):
δ 0.8-1.1(b, —NHCH(CH(C̲H̲₃)CH₂CH₃)COOCH₂CH₃),
δ 1.1-1.4(b, —NHCH(CH(CH₃)C̲H̲₂CH₃)COOCH₂C̲H̲₃),
δ 1.4-1.8(b, —NHC̲H̲(CH(CH₃)CH₂CH₃)COOCH₂CH₃),
δ 1.52-1.64(b, —NHCH₂CH₂OCOCH₂ C̲H̲₂C̲H̲₂CH₂COOH),
δ 2.3-2.32(b, —NHCH₂CH₂OCOC̲H̲₂CH₂CH₂ C̲H̲₂COOH),
δ 2.67-3.2(b, —NHCH₂C̲H̲₂OH, —NH(CH₂CH₂O)₁₆ C̲H̲₃),
δ 3.4(s, —NH(CH₂CH₂O)₁₆C̲H̲₃),
δ 3.4-3.9(b, —NH(C̲H̲₂C̲H̲₂O)₁₆CH₃, —NH C̲H̲(CH(CH₃)CH₂CH₃)COOCH₂CH₃),
δ 3.9-4.3(b, —NHCH(CH(CH₃)CH₂CH₃)COOC̲H̲₂CH₃, —NHCH₂C̲H̲₂OCOCH₂CH₂CH₂COOH),
Average molecular weight ($M_w$): 4430

Experimental Example 1

Sol-Gel Change of Sulfate Group-Containing Phosphazene-Based Polymer According to Temperature Change Each of the phosphazene-based polymers including or not including a sulfate group prepared according to Examples 1 to 18 and Comparative Examples 1 to 4 was dissolved in phosphate-buffered saline (pH 7.4) at 4° C. at a concentration of 10 wt %. Then, the resultant was placed in a chamber of a viscometer (Brookfield DV-III+ Rheometer) equipped with an automatic water distiller TC-501, and a sol-bel transition behavior thereof was observed at a shear rate of 0.1 to 1.7 per second while raising a temperature by 0.33° C. per minute.

FIG. 1 shows photographs of the solution of the sulfate group-containing phosphazene-based polymer prepared in Example 3 dissolved in phosphate-buffered saline (pH 7.4) at 4° C. at a concentration of 10 wt % obtained by visual observation of the sol-gel behavior thereof. It was confirmed that the solution state was maintained at a temperature below the initial gelation temperature and turned to a gel state at a temperature higher than the body temperature of 37° C.

In addition, gel properties of the polymers according to Examples 1 to 18 and Comparative Examples 1 to 4 with respect to temperature are shown in Table 1 below.

have different initial gelation temperatures and strengths according to the ratio of respective substituents.

Figure 3:
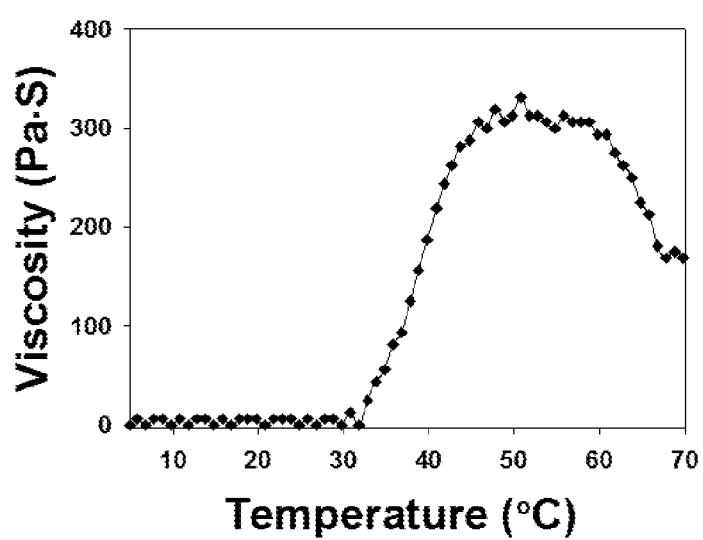

Furthermore, viscosities of the solutions of the sulfate group-containing phosphazene-based polymers (Examples 3 and 11) according to the present invention dissolved in phosphate-buffered saline (pH 7.4) at 4° C. at a concentration of 10 wt % were measured with respect to temperature and the results are shown in FIGS. 2 and 3. A state flowing fast like water was observed from a low temperature to room temperature since the viscosity thereof was 0, and a state flowing slow unlike water was observed at around the body temperature due to an increase in the viscosity. In general, a gel state that does not flow in the direction of gravity was observed at a viscosity of 100 Pa·s or greater, and thus it was confirmed that the state was changed to a gel state.

Experimental Example 2

Surface Charge Change of Sulfate Group-Containing Phosphazene-Based Polymer

In order to measure surface charges of the sulfate group-containing phosphazene-based polymers according to the present invention, each of the polymers was dissolved in phosphate-buffered saline (pH 7.4) at a concentration of 1 wt % and a Zeta-potential thereof was measured (Zetasizer Nano ZS, Malvern instrunets Ltd., Malvernm UK). Various

TABLE 1

| Polymer | Structure | Initial gelation temperature (° C.) | Gel strength at body temperature (Pa·s) |
|---|---|---|---|
| Example 1 | $[NP(IleOEt)_{1.38}(AMPEG750)_{0.57}(AEs)_{0.05}]_n$ | 16 | 325 |
| Example 2 | $[NP(IleOEt)_{1.35}(AMPEG750)_{0.50}(AEs)_{0.15}]_n$ | 20 | 368.7 |
| Example 3 | $[NP(IleOEt)_{1.32}(AMPEG750)_{0.38}(Aminoethanol)_{0.10}(AES)_{0.20}]_n$ | 28 | 145 |
| Example 4 | $[NP(IleOEt)_{1.23}(AMPEG550)_{0.57}(AEs)_{0.20}]_n$ | 13 | 300 |
| Example 5 | $[NP(IleOEt)_{1.21}(AMPEG550)_{0.51}(AEs)_{0.28}]_n$ | 20 | 232.5 |
| Example 6 | $[NP(IleOEt)_{1.25}(AMPEG550)_{0.45}(Aminoethanol)_{0.12}(AEs)_{0.18}]_n$ | 20 | 292.5 |
| Example 7 | $[NP(IleOEt)_{1.38}(AMPEG750)_{0.40}(GlyLacOEt)_{0.02}(AEs)_{0.20}]_n$ | 15 | 580 |
| Example 8 | $[NP(IleOEt)_{1.23}(AMPEG550)_{0.43}(GlyLacOEt)_{0.04}(AEs)_{0.3}]_n$ | 23 | 255 |
| Example 9 | $[NP(IleOEt)_{1.38}(AMPEG750)_{0.32}(AEs)_{0.15}(Aminoethylsuccinate)_{0.15}]_n$ | 28 | 245 |
| Example 10 | $[NP(IleOEt)_{1.22}(AMPEG550)_{0.50}(AEs)_{0.10}(Aminoethylsuccinate)_{0.18}]_n$ | 22 | 175 |
| Example 11 | $[NP(IleOEt)_{1.39}(AMPEG750)_{0.31}(AEs)_{0.13}(AminoethylGlutarate)_{0.17}]_n$ | 32 | 181 |
| Example 12 | $[NP(IleOEt)_{1.21}(AMPEG550)_{0.49}(AEs)_{0.20}(AminoethylGlutarate)_{0.1}]_n$ | 25 | 125 |
| Example 13 | $[NP(IleOEt)_{1.36}(AMPEG750)_{0.28}(AEs)_{0.21}(AminoethylAdipate)_{0.15}]_n$ | 29 | 400 |
| Example 14 | $[NP(IleOEt)_{1.21}(AMPEG550)_{0.49}(AEs)_{0.12}(AminoethylAdipate)_{0.18}]_n$ | 19 | 456.5 |
| Example 15 | $[NP(IleOEt)_{1.40}(AMPEG750)_{0.3}(AEs)_{0.16}(AminoethylAdipate)_{0.14}]_n$ | 31 | 251 |
| Example 16 | $[NP(IleOEt)_{1.41}(AMPEG750)_{0.40}(AEs)_{0.12}(AminoethylsuccinateImidazole)_{0.07}]_n$ | 30 | 230 |
| Example 17 | $[NP(IleOEt)_{1.49}(AMPEG750)_{0.34}(AEs)_{0.10}(AminoethylsuccinateCRRRRHHHHHGGGGGRGDS)_{0.07}]_n$ | 28 | 270 |
| Example 18 | $[NP(IleOEt)_{1.4}(AMPEG750)_{0.30}(AEMAEs)_{0.16}(AminoethylMethacylate)_{0.14}]_n$ | 18 | 325 |
| Comparative Example 1 | $[NP(IleOEt)_{1.26}(AMPEG750)_{0.44}(Aminoethanol)_{0.36}]_n$ | 10 | 206 |
| Comparative Example 2 | $[NP(IleOEt)_{1.32}(AMPEG750)_{0.32}(Aminoethylsuccinate)_{0.36}]_n$ | 16 | 662 |
| Comparative Example 3 | $[NP(IleOEt)_{1.48}(AMPEG750)_{0.41}(AminoethylGlutarate)_{0.11}]_n$ | 19 | 893.7 |
| Comparative Example 4 | $[NP(IleOEt)_{1.33}(AMPEG750)_{0.44}(AminoethylAdipate)_{0.23}]$ | 23 | 225 |

In Table 1 above, the term 'initial gelation temperature' refers to a temperature where a viscosity of an aqueous solution of the polymer (a viscosity of 2 Pa·s or lower when measured by a viscometer) starts to gradually increase, specifically, a temperature where a viscosity measured by the viscometer is 10 Pa·s or higher, and the term 'gel strength at body temperature' refers to a strength of a polymer gel measured at 37° C.

As shown in Table 1, it was confirmed that the polymers consisting of the same substituents (Examples 1 and 2) may biologically effective factors may be retained in a hydrogel of the polymer and sustained-release thereof may be achieved due to ionic interactions according to types and degrees of surface charges of the polymers.

Figure 4:
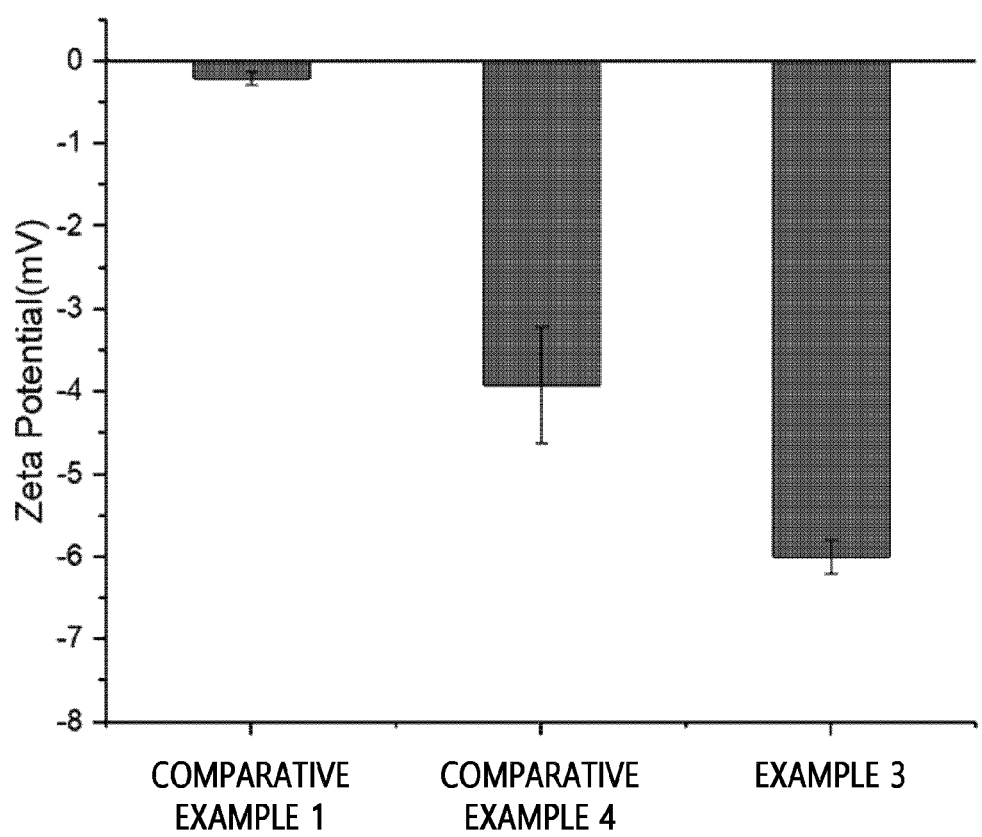
FIG. 4 is a graph illustrating surface charges of a hydroxy group-containing phosphazene-based polymer (Comparative Example 1) as a matrix polymer, a phosphazene-based polymer substituted with a carboxyl group (Comparative Example 4), and a phosphazene-based polymer substituted with a sulfate group (Example 3).

In order to observe changes in surface charges caused by introduction of the sulfate group, surface charges of a hydroxy group-containing phosphazene-based polymer (Comparative Example 1) as a matrix polymer of the sulfate group-containing phosphazene polymer, the phosphazene-based polymer substituted with a carboxyl group (Comparative Example 4), and a sulfate group-containing phosphazene polymer (Example 3) were respectively measured and the results are shown in FIG. 4. As shown in Table 1, when the total amount of substituents is considered as 2, amounts of anionic group-containing substituents of the phosphazene-based polymers according to Comparative Example 1, Comparative Example 4, and Example 3 were 0, 0.26, and 0.2, respectively. Referring to FIG. 4, the polymers prepared according to Comparative Example 1, Comparative Example 4, and Example 3 exhibited zeta potentials of −0.21 mV, −3.93 mV, and −6.23 mV, respectively, indicating that the polymer including the sulfate group has a stronger negative charge although it has fewer substituents.

Figure 5:
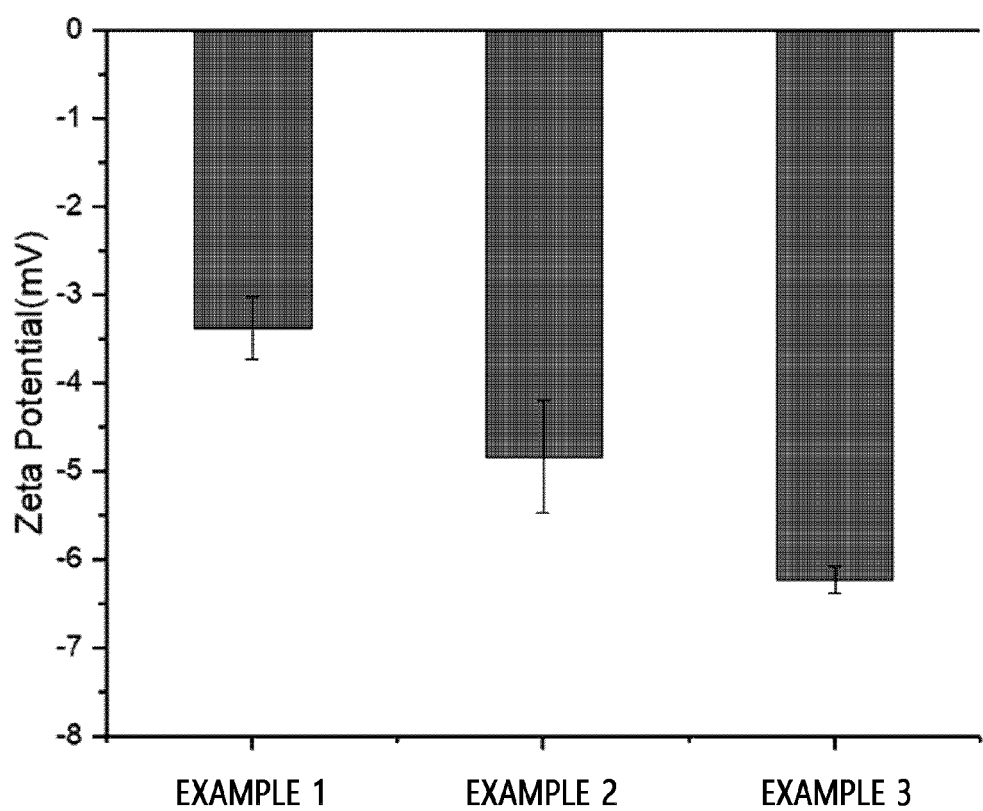
FIG. 5 is a graph illustrating changes in surface charges of phosphazene-based polymers (Examples 1, 2, and 3) according to a substitution degree of the sulfate group.

Furthermore, in order to measure changes in surface charges of the polymers according to a substitution degree of the sulfate group, surface charges of the group-containing phosphazene-based polymers prepared as described above were measured and shown in FIG. 5. When the total amount of substituents is considered as 2, amounts of the sulfate groups of the phosphazene-based polymers according to Examples 1, 2, and 3 were 0.05, 0.15, and 0.2 respectively. Surface charges of the polymers according to Examples 1, 2, and 3 were measured as −3.38 mV, −4.83 mV, and −6.23 mV, respectively, indicating that surface charge varies according to the amount of the sulfate group.

Experimental Example 3

Observation of In Vivo Gelation and Biodegradability by Injection of Aqueous Solution of Sulfate Group-Containing Phosphazene Polymer In order to identify an in vivo degradation rate of the sulfate group-containing phosphazene-based polymer hydrogel, changes in amounts of the polymer hydrogel over time were measured after injection into mice. Specifically, the sulfate group-containing phosphazene-based polymer according to Example 3 was dissolved in phosphate-buffered saline (pH 7.4) at a concentration of 10 wt % and loaded into a 31G syringe and then subcutaneously injected into the mice. A subcutaneous area was excised over time, and changes in residual amounts of the sulfate group-containing phosphazene-based polymer were measured. The results are shown in FIG. 6.

Experimental Example 4

Evaluation of Cytotoxicity of Sulfate Group-Containing Phosphazene Polymer

Figure 7:
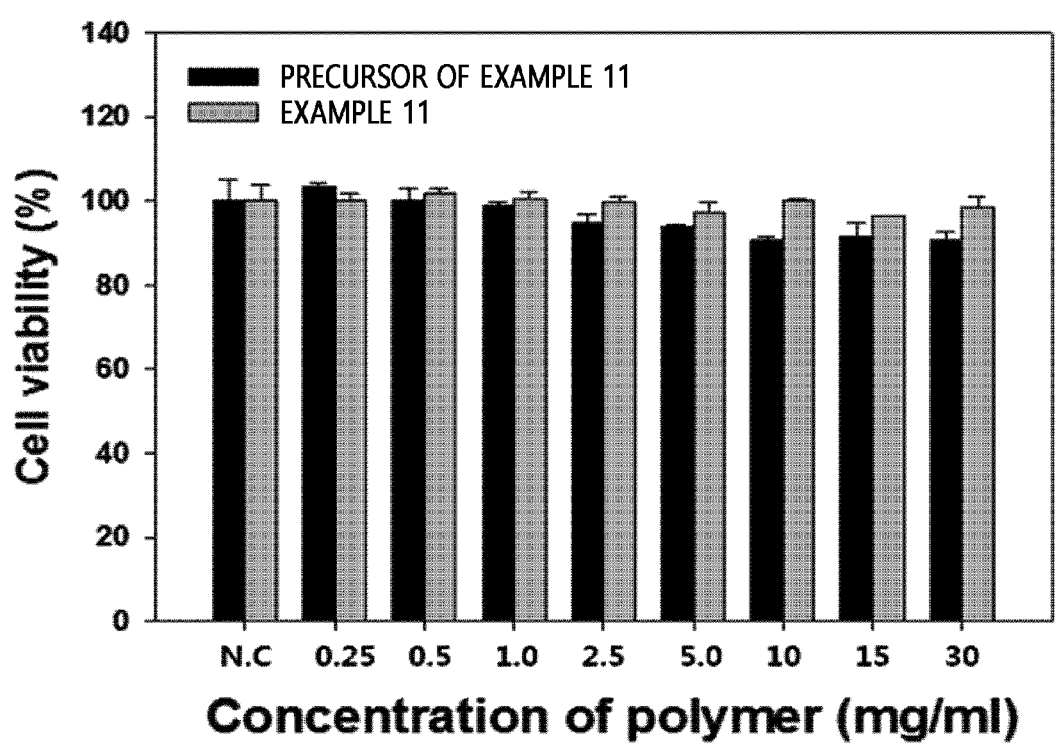
FIG. 7 is a graph illustrating comparison results of cytotoxicity between a sulfate group-containing polyphosphazene-based polymer of Example 11 and a precursor polymer immediately before introducing the sulfate group thereinto.

In order to evaluate cytotoxicity of the sulfate group-containing polyphosphazene-based polymer, the polymer was dissolved in a cell culture at a concentration of up to 30 mg/ml and added to a 96 well plate in which 10,000 Fibroblast (NIH3T3) cells were distributed at different concentrations. The cells were cultured overnight or more and cell viability was measured to evaluate cytotoxicity of the sulfate group-containing polyphosphazene-based polymer, and the results are shown in FIG. 7. By simultaneously evaluating the sulfate group-containing polyphosphazene-based polymer according to Example 11 and a precursor polymer immediately before introducing the sulfate group thereinto, it was proved that cytotoxicity was prevented by introducing the sulfate group. Interestingly, it was found that the sulfate group contained in the hydrogel of the phosphazene-based polymer alleviated cytotoxicity although the polyphosphazene-based polymer was used at a high concentration.

Experimental Example 5

Figure 8:
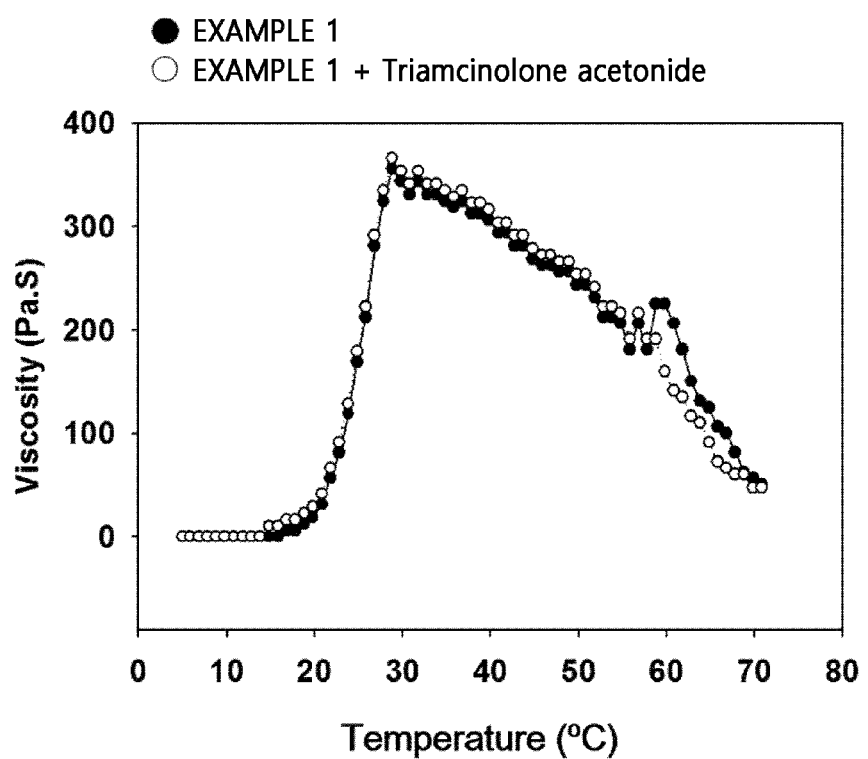
FIG. 8 is a graph illustrating changes in viscosity of an aqueous solution including a phosphazene-based polymer according to Example 1 and triamcinolone acetonide with respect to temperature.

Observation of Sol-Gel Transition of Aqueous Solution of Sulfate Group-Containing Phosphazene-Based Polymer Including Synthetic Drug According to Temperature Change In order to identify the possibility of the phosphazene-based polymer according to the present invention as a drug carrier, an aqueous solution of the polymer loaded with a synthetic drug was prepared, gel properties thereof according to temperature change were observed, and the results are shown in FIG. 8. In FIG. 8, viscosity of a solution prepared by dissolving the sulfate group-containing phosphazene-based polymer according to Example 1 in phosphate-buffered saline (pH 7.4) at 4° C. at a concentration of 10 wt % and viscosity of a solution prepared by further dissolving Triamcinolone acetonide (synthetic corticosteroid for intra-articular use) in the same solution at a concentration of 1 wt % according to temperature were shown.

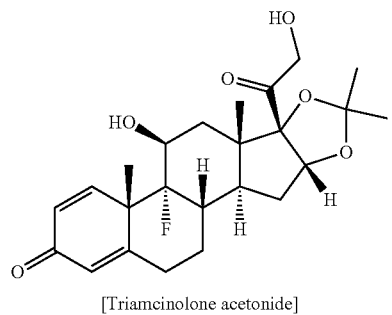

[Triamcinolone acetonide]

Experimental Example 6

Figure 9:
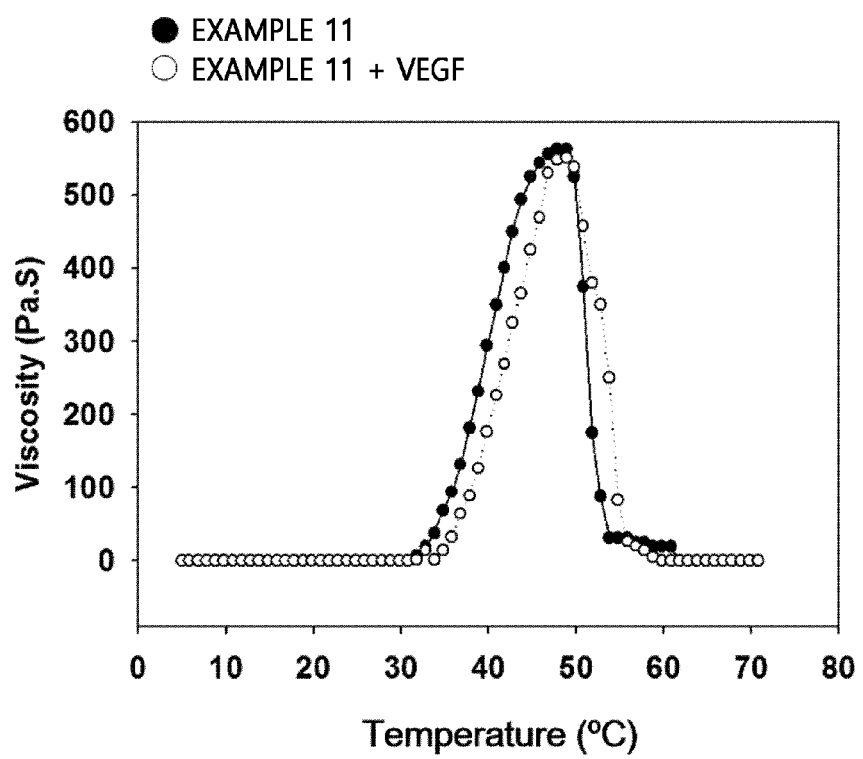
FIG. 9 is a graph illustrating changes in viscosity of an aqueous solution including a phosphazene-based polymer according to Example 11 and a vascular endothelial growth factor (VEGF) with respect to temperature.

Observation of Sol-Gel Transition of Sulfate Group-Containing Phosphazene-Based Polymer Including Protein Drug According to Temperature Change In order to identify the possibility of the phosphazene-based polymer according to the present invention as a drug carrier, an aqueous solution of the polymer loaded with a protein drug was prepared, gel properties thereof according to temperature change were observed, and the results are shown in FIG. 9. In FIG. 9, viscosity of a solution prepared by dissolving the sulfate group-containing phosphazene-based polymer according to Example 11 in phosphate-buffered saline (pH 7.4) at 4° C. at a concentration of 10 wt % and viscosity of a solution prepared by further dissolving vascular endothelial growth factor (VEGF) in the same solution at a concentration of 50 μg/ml according to temperature were shown.

Experimental Example 7

Observation of In Vitro Releasing Behavior of Vascular Endothelial Growth Factor (VEGF) from Sulfate Group-Containing Phosphazene-Based Polymer Hydrogel 50 μg of a vascular endothelial growth factor (VEGF) was added to 1 mL of a solution prepared by dissolving the phosphazene-based polymer according to Example 11 in phosphate-buffered saline at a concentration of 10 wt %, and then 300 μl of the mixture was loaded on a milli cell, followed by formation of a hydrogel at 37° C. The phosphazene-based polymer hydrogel loaded with the vascular endothelial growth factor (VEGF) was added to 6 mL of a release solution (phosphate-buffered saline, pH 7.4) and stirred at 37° C. in a water bath at 50 rpm, and the release solution was replaced with 6 mL of a new release solution at a predetermined time. The released vascular endothelial growth factor (VEGF) was quantified by analyzing the release solution collected at a predetermined time using an ELIZA KIT.

Figure 10:
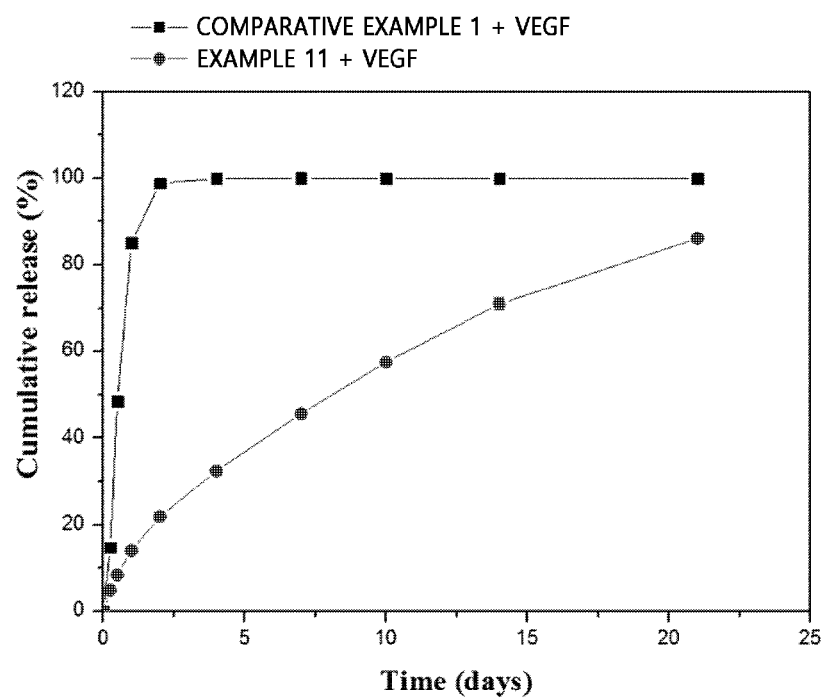
FIG. 10 is a graph illustrating release behaviors of a vascular endothelial growth factor (VEGF) from phosphazene-based polymer hydrogels according to Example 11 and Comparative Example 1 with time.

A release behavior of the vascular endothelial growth factor (VEGF) from the phosphazene-based polymer hydrogel over time is shown in FIG. 10. As shown in FIG. 10, while the phosphazene-based polymer hydrogel not including the sulfate group did not inhibit initial release of the vascular endothelial growth factor (VEGF), it was confirmed that the sulfate group-containing phosphazene-based polymer hydrogel efficieintly inhibited an excessive release of the vascular endothelial growth factor (VEGF) loaded thereon at the initial stage and the release was controlled for a long time. This may be understood because the vascular endothelial growth factor may be trapped in the hydrogel for a long time due to ionic interactions between the vascular endothelial growth factor (VEGF) cationic at pH 7.4 and the sulfate group-containing phosphazene-based polymer anionic in the same environment.

Experimental Example 8

Observation of In Vitro Release Behavior of Stromal Cell-Derived Factor-1 (SDF-1) from Sulfate Group-Containing Phosphazene-Based Polymer Hydrogel 50 μg of a stromal cell-derived factor-1 (SDF-1) was added to 1 mL of a solution prepared by dissolving the phosphazene-based polymer according to Example 11 in phosphate-buffered saline at a concentration of 10 wt %, and then 300 μl of the mixture was loaded on a milli cell, followed by formation of a hydrogel at 37° C. The phosphazene-based polymer hydrogel loaded with the stromal cell-derived factor-1 (SDF-1) was added to 6 mL of a release solution (phosphate-buffered saline, pH 7.4) and stirred at 37° C. in a water bath at 50 rpm, and the release solution was replaced with 6 mL of a new release solution at a predetermined time. The released stromal cell-derived factor-1 (SDF-1) was quantified by analyzing the release solution collected at a predetermined time using an ELIZA KIT.

Figure 11:
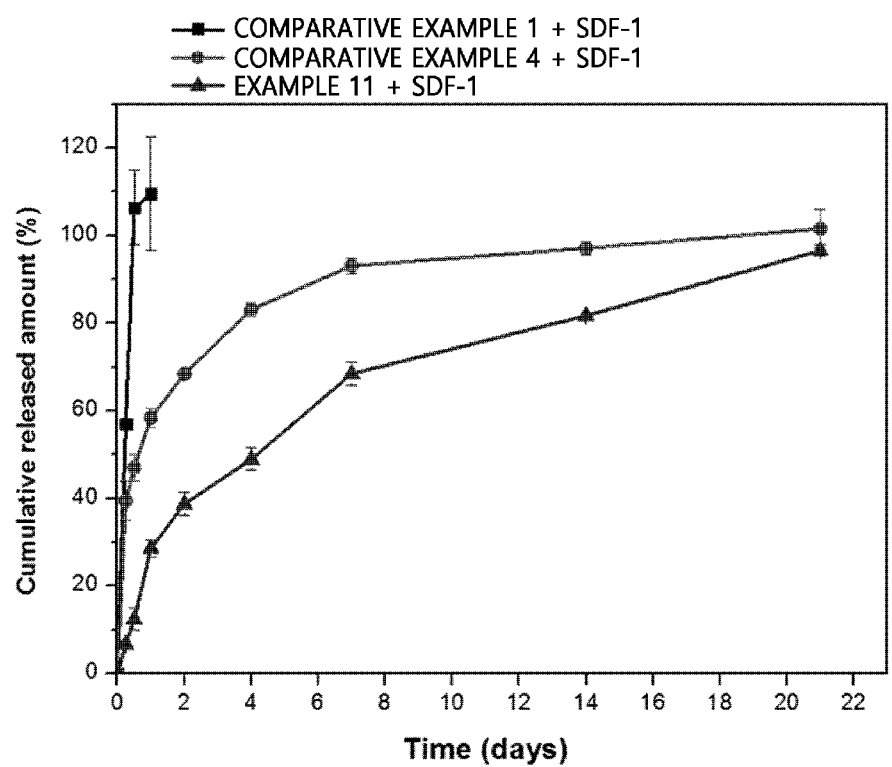
FIG. 11 is a graph illustrating release behaviors of a stromal cell-derived factor from phosphazene-based polymer hydrogels according to Example 11 and Comparative Examples 1 and 4 with time.
Figure 12:
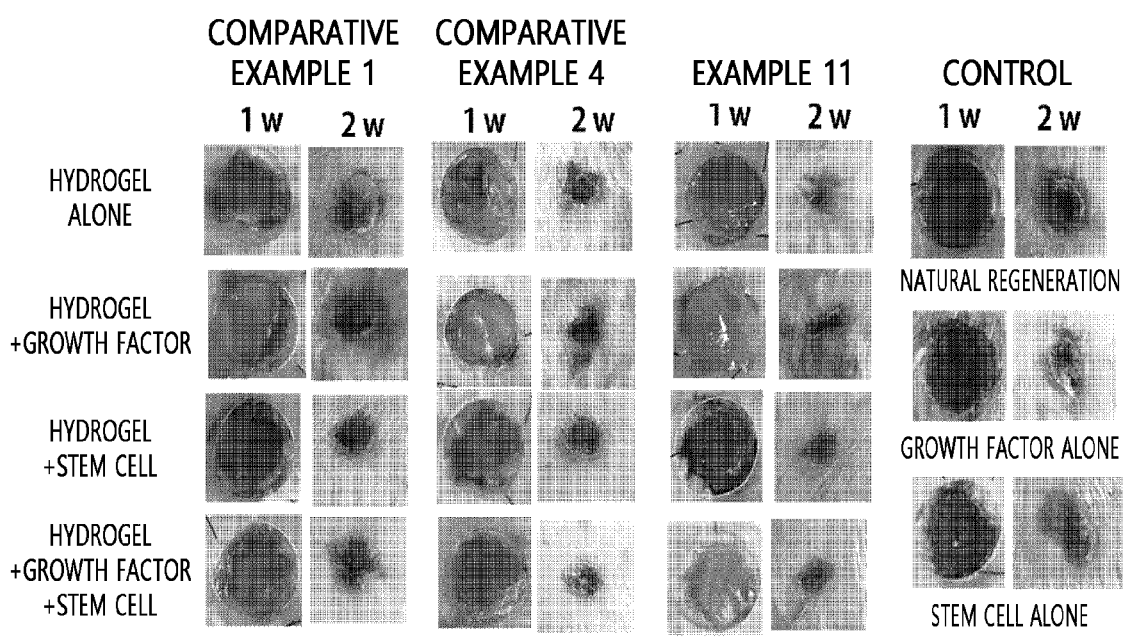
FIGS. 12 to 16 shows comparison results of tissue regeneration effects among hydrogels formed of phosphazene-based polymers according to Example 11 and Comparative Examples 1 and 4 alone, hydrogels formed of each of the polymers and a growth factor, hydrogels formed of each of the polymers and a stem cell, hydrogels formed of the polymer and both, natural regeneration, a growth factor alone without hydrogel, or a stem cell alone without hydrogel.
Figure 13:
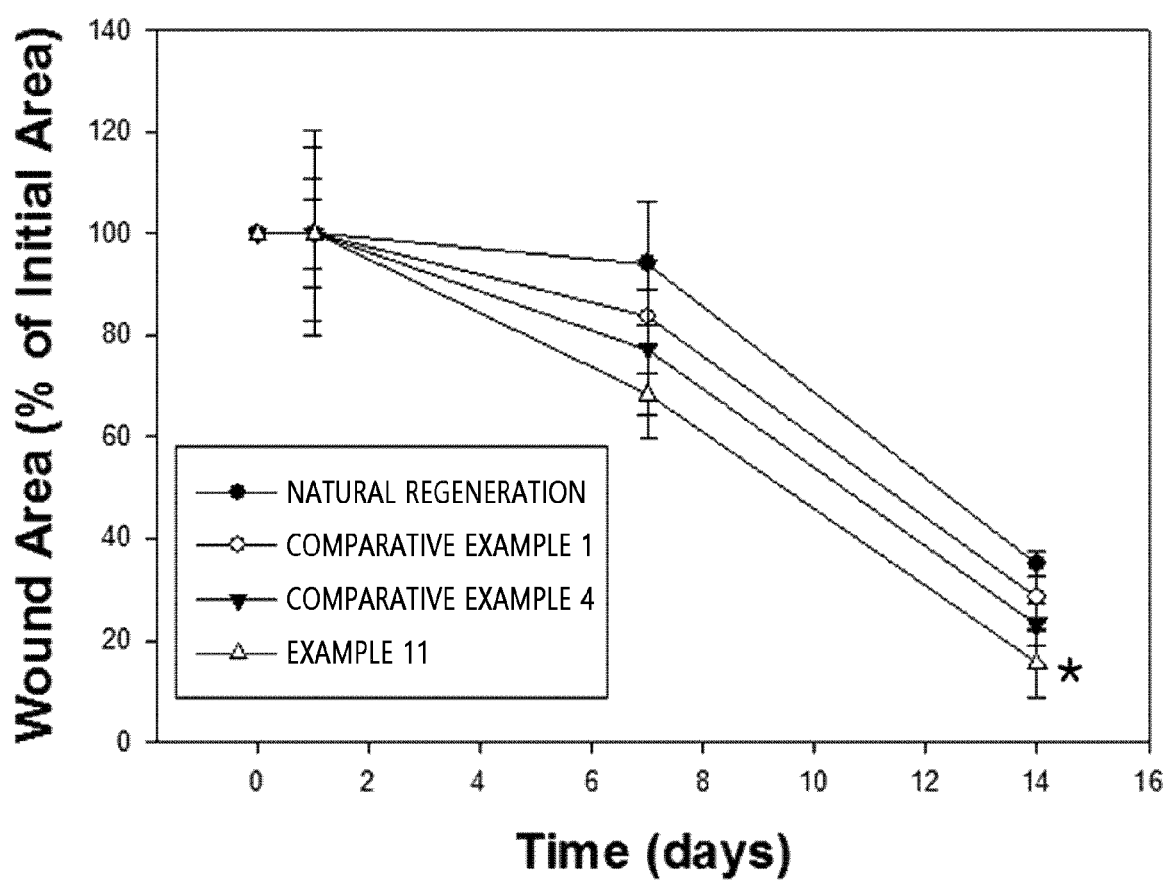
Figure 14:
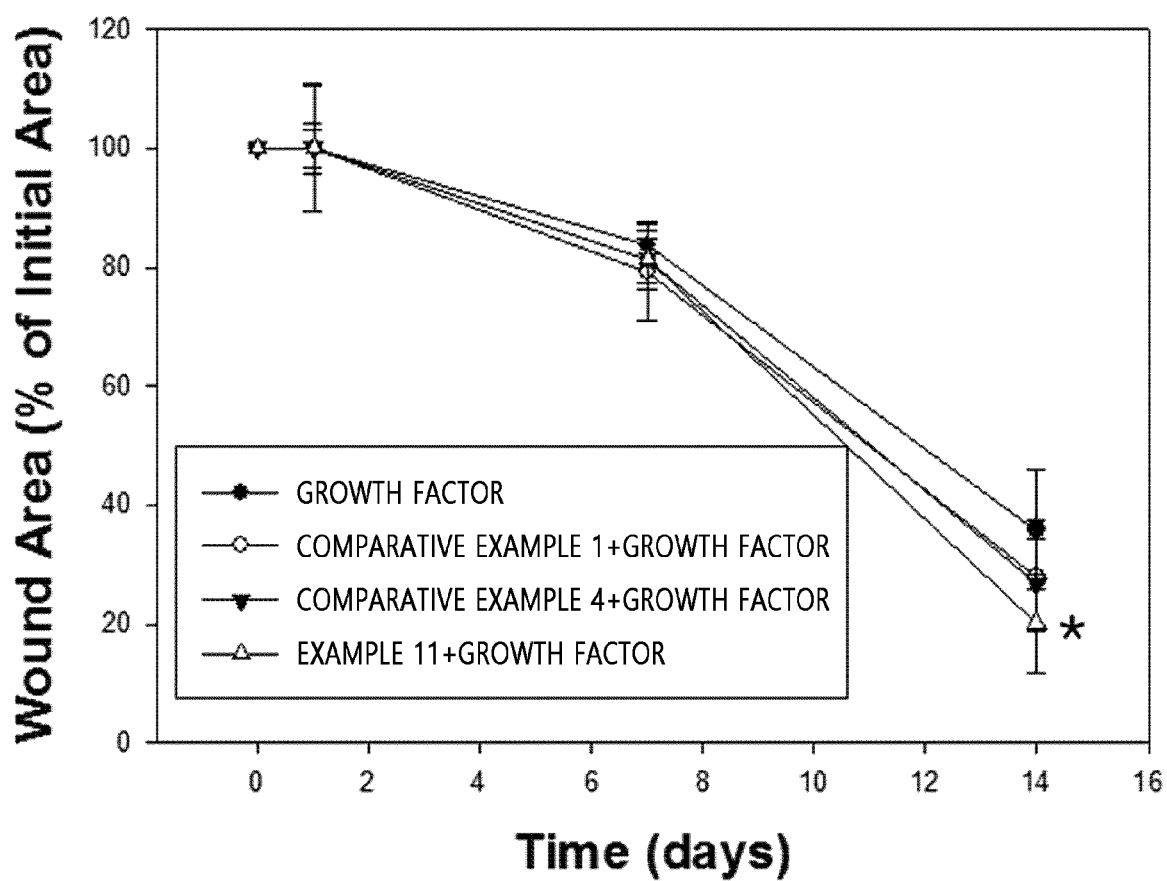
Figure 15:
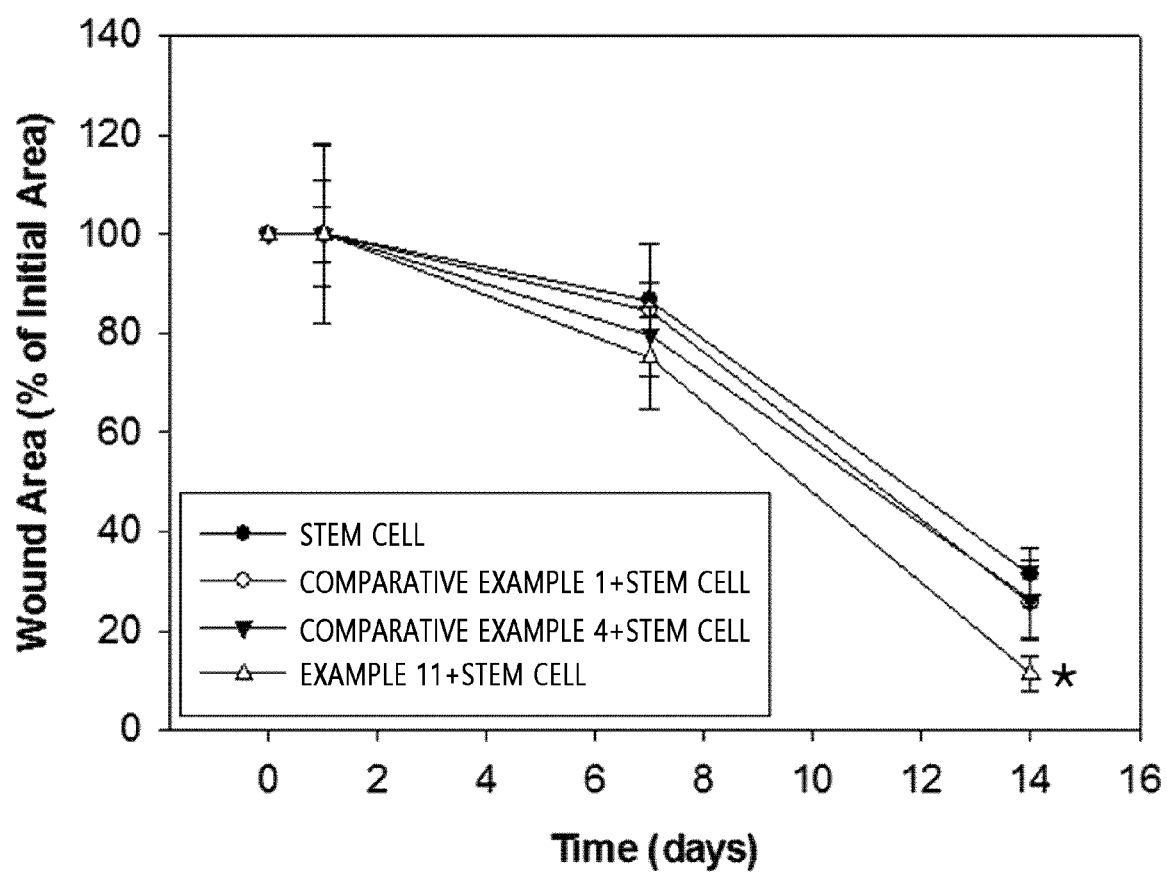
Figure 16:
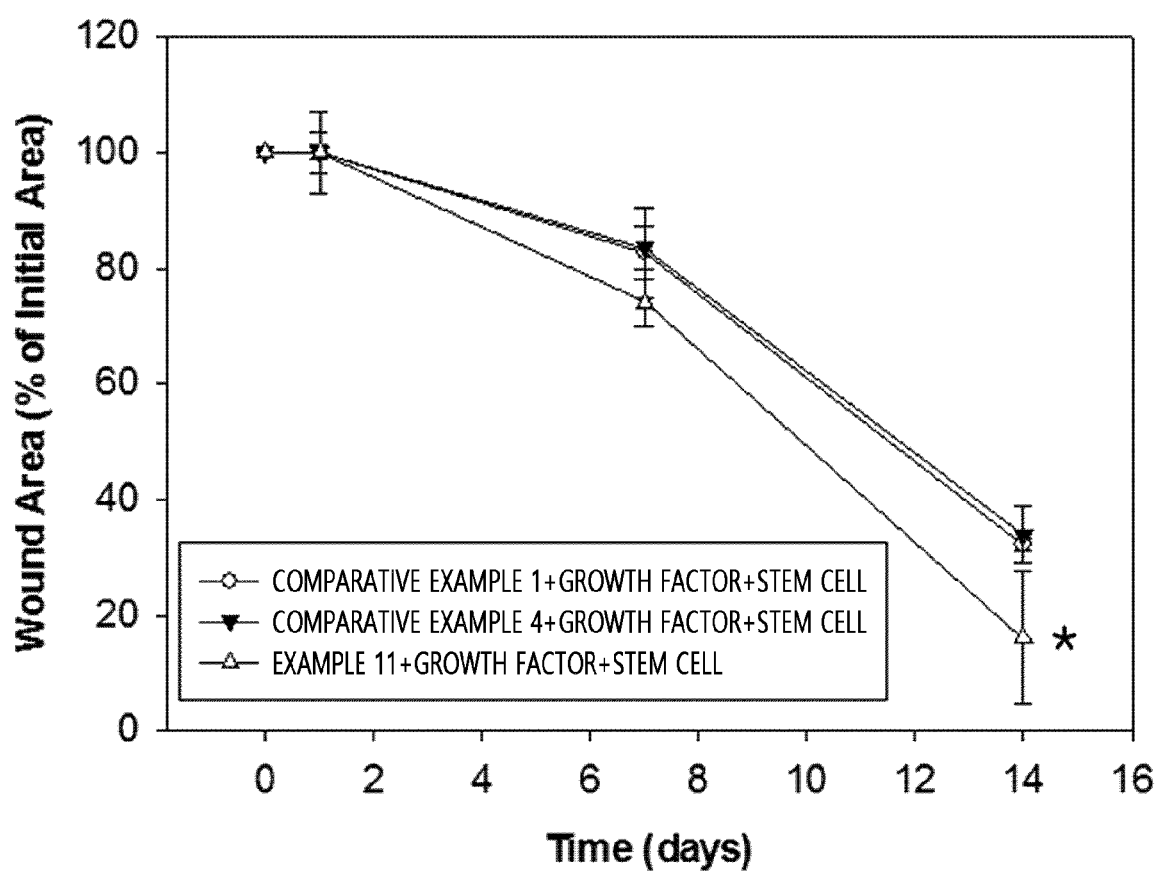

A release behavior of the stromal cell-derived factor-1 (SDF-1) from the phosphazene-based polymer hydrogel over time is shown in FIG. 11. As shown in FIG. 11, while the phosphazene-based polymer hydrogel not including the sulfate group did not inhibit initial release of the stromal cell-derived factor-1 (SDF-1), the carboxyl group-containing phosphazene-based polymer hydrogel controlled the release behavior of the stromal cell-derived factor-1 (SDF-1) relatively well. In this case, the sulfate group-containing phosphazene-based polymer hydrogel showed a far less initial release amount than the previous release patterns observed in Comparative Examples 1 and 4. This may be understood because the stromal cell-derived factor-1 (SDF-1) may be trapped in the hydrogel for a long time due to ionic interactions between the stromal cell-derived factor-1 (SDF-1) cationic in the pH 7.4 environment and the sulfate group-containing phosphazene-based polymer anionic in the same environment.

Experimental Example 9

Evaluation of Skin Regeneration Effect of Sulfate Group-Containing Polyphosphazene-Based Polymer in Skin-Damaged Animal Model of Mice The sulfate group-containing phosphazene-based polymer prepared according to Example 11 was dissolved in phosphate-buffered saline at a concentration of 10 wt % and mice having severe skin damage on the back were treated with the solution to evaluate self-skin regeneration efficacy. The sulfate group-containing polyphosphazene-based polymer hydrogel alone may promote the skin regeneration. Even when a biologically effective factor or a stem cell was added thereto, skin regeneration may also be promoted due to improved abilities to store the biologically effective factor or to deliver the biologically effective factor to the damaged region. Efficacy of the sulfate group-containing phosphazene-based polymer hydrogel is shown in more detail in FIGS. 12, 13, 14, 15, and 16. When skin regeneration of damaged areas was induced using the hydrogel according to Example 11 as shown in FIGS. 12, 13, 14, 15, and 16, statistically significant (*$p<0.05$) regeneration effects were observed when compared with the comparative examples without using the hydrogel and the polymer of Comparative Example 1.

In short, the phosphazene-based polymer according to the present invention may efficiently introduce a biologically effective factor into a hydrogel via a sulfate group to promote migration, growth, and differentiation of cells, thereby exhibiting superior regeneration efficacy when compared with natural regeneration or the polymer hydrogels according to Comparative Examples 1 and 4.

The invention claimed is:
1. A thermosensitive phosphazene-based polymer comprising:
   a first moiety of an amino acid ester represented by Formula 2;
   a second moiety of polyethyleneglycol represented by Formula 3; and
   a third moiety including a sulfate group;
   wherein the first moiety, the second moiety, and the third moiety are linked by an amino nitrogen to a phosphorous atom of a polyphosphazene backbone represented by Formula 1; and
   wherein the mole percent range of the first moiety, the second moiety, and the third moiety present in the phosphazene-based polymer are represented by a, b, and c, respectively,

[Formula 1]

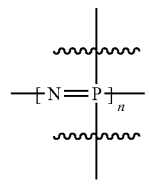

-continued

[Formula 2]
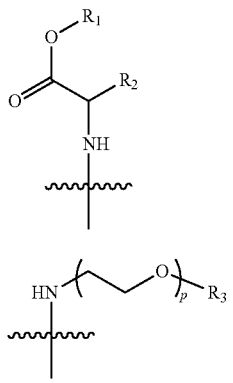

[Formula 3]

wherein a is 55 mol % to 75 mol %, b is 5 mol % to 30 mol %, and c is 0.5 mol % to 20 mol %, and
in Formulae 1, 2, and 3,
$R_1$ is $C_{1-6}$ alkyl, $C_{1-6}$ alkenyl, or $C_{6-10}$ aryl-$C_{1-6}$ alkyl;
$R_2$ is hydrogen, methyl, isopropyl, 1-methylpropyl, 2-methylpropyl, thiomethyl, methylthioethyl, benzyl, hydroxybenzyl, or 2-indolylmethyl;
$R_3$ is $C_{1-6}$ alkyl;
n is an integer of 3 to 100,000; and
p is an integer of 1 to 20.

2. The thermosensitive phosphazene-based polymer according to claim 1, wherein $R_1$ is methyl, ethyl, propyl, butyl, benzyl, or 2-prophenyl; and $R_3$ is methyl.

3. The thermosensitive phosphazene-based polymer according to claim 1, further comprising a fourth moiety including a functional moiety for introducing a functional group into an end of the polymer.

4. The thermosensitive phosphazene-based polymer according to claim 3, further comprising a fourth moiety including at least one functional substance linked directly or by a linker to a part of or the entire functional group of the fourth moiety, wherein the functional substance; is capable of regulating a degradation rate of the polymer, a is capable of cross-linking, is capable of inducing tissue adhesion, a physiologically active substance, or a composite material formed by linear connection of two or more substances thereof.

5. The thermosensitive phosphazene-based polymer according to claim 1, wherein the phosphazene-based polymer including a sulfate group is represented by a formula of poly[(isoleucineethylester)$_a$(aminomethoxypolyethyl-eneglycol 750)$_b$(aminoethylsulfate)$_c$phosphazene]$_{n'}$:
wherein in the formula,
a' is 1.1 to 1.5;
b' is 0.1 to 0.6;
c' is 0.01 to 0.4,
1.6≤a'+b'+c'≤2, and
n' is an integer of 3 to 100,000.

6. A method of preparing the phosphazene-based polymer including a sulfate group according to claim 1, the method comprising:
a first step of reacting polydichlorophosphazene represented by Formula 4 with an amino acid ester represented by Formula 5;
a second step of further reacting the reaction mixture obtained from the first step by adding a $C_{1-6}$ aminoalkanol or a hydrogen sulfate compound including an amine group at one end to the reaction mixture;
a third step of further reacting the reaction mixture obtained from the second step by adding aminopoly-ethyleneglycol to the reaction mixture; and
a fourth step of reacting a product obtained from the third step with a sulfur trioxide or a composite thereof:

[Formula 4]
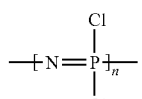

[Formula 5]
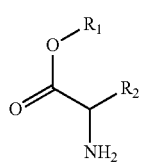

wherein in Formulae 4 and 5,
$R_1$, $R_2$ and n are as defined in claim 1,
wherein the second step and the third step are able to be performed in a reverse order, and
the fourth step is omitted when the hydrogen sulfate compound including an amine group at one end is added in the second step.

7. The method according to claim 6, wherein the sulfur trioxide is used in the form of a composite with a tertiary amine-based compound in the fourth step.

8. A hydrogel-forming composition comprising a thermosensitive phosphazene-based polymer, the phosphazene-based polymer comprising:
a first moiety of an amino acid ester represented by Formula 2;
a second moiety of polyethyleneglycol represented by Formula 3; and
a third moiety including a sulfate group;
wherein the first moiety, the second moiety, and the third moiety are linked by an amino nitrogen to a phosphorous atom of a polyphosphazene backbone represented by Formula 1; and
wherein the mole percent of the first moiety, the second moiety, and the third moiety present in the phosphazene-based polymer are represented by a, b, and c, respectively, Formula 1
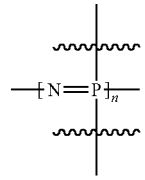

Formula 2
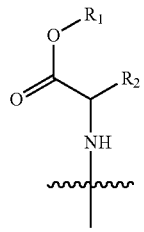

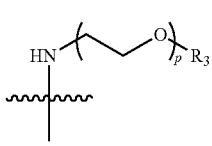
Formula 3 wherein a is 55 mol % to 75 mol %, b is 5 mol % to 30 mol %, and c is 0.5 mol % to 20 mol %, and
in Formulae 1, 2, and 3,
$R_1$ is $C_{1-6}$ alkyl, $C_{1-6}$ alkenyl, or $C_{6-10}$ aryl-$C_{1-6}$ alkyl;
$R_2$ is hydrogen, methyl, isopropyl, 1-methylpropyl, 2-methylpropyl, thiomethyl, methylthioethyl, benzyl, hydroxybenzyl, or 2-indolylmethyl;
$R_3$ is $C_{1-6}$ alkyl;
n is an integer of 3 to 100,000; and
p is an integer of 1 to 20.

9. The hydrogel-forming composition according to claim 8, wherein the hydrogel-forming composition is converted from a sol state to a gel state by body temperature to form a hydrogel in the body.

10. The hydrogel-forming composition according to claim 9, further comprising a substance that is present in the hydrogel in the body.

11. The hydrogel-forming composition according to claim 10, wherein the hydrogel formed in the body releases the substance to the body.

12. The hydrogel-forming composition according to claim 9, wherein the hydrogel in the body absorbs water, an inorganic ion, a vitamin, a hormone, or a growth factor.

13. The hydrogel-forming composition according to claim 8, wherein the phosphazene-based polymer further comprises a carboxyl group.

14. The hydrogel-forming composition according to claim 8, wherein the hydrogel assists tissue regeneration.

15. The hydrogel-forming composition according to claim 8, wherein the hydrogel serves as a body tissue prosthesis.

16. A hydrogel formed from the hydrogel-forming composition according to claim 8.

17. The hydrogel according to claim 16, wherein the hydrogel is used as a filter to control passage of molecules or particles in a body.

18. The hydrogel according to claim 16, wherein water, an inorganic ion, a vitamin, or a hormone is stored in a gel.

19. The thermosensitive phosphazene-based polymer according to claim 1, wherein a is 60.5 mol % to 69 mol %, b is 19 mol % to 28.5 mol %, and c is 2.5 mol % to 15 mol %.

* * * * *